United States Patent [19]
> Paik et al.

[11] Patent Number: 5,869,476
[45] Date of Patent: Feb. 9, 1999

[54] PYRIMIDINONE DERIVATIVES

[75] Inventors: Woo Hyun Paik, Kyugki-do; Ji Han Kim, Seoul; Jae Hyoung Lee, Kyungki-do; Kyung Jin Jang, Kyungki-do; Kwang Jae Cho, Kyungki-do; Jae Seog Kang, Seoul; Byoung Wug Yoo, Daejun; Je Bum Park, Seoul; Kyung Jin Kim; Kun Ja Lee, both of Kyungki-do, all of Rep. of Korea

[73] Assignee: Boryung Pharmaceutical Co., Ltd., Seoul, Rep. of Korea

[21] Appl. No.: 809,314

[22] PCT Filed: Sep. 15, 1995

[86] PCT No.: PCT/KR95/00121

§ 371 Date: Apr. 25, 1997

§ 102(e) Date: Apr. 25, 1997

[87] PCT Pub. No.: WO96/08476

PCT Pub. Date: Mar. 21, 1996

[30] Foreign Application Priority Data

Sep. 17, 1994 [KR] Rep. of Korea ............... 1994 23941
Feb. 13, 1995 [KR] Rep. of Korea ................ 1995 2565

[51] Int. Cl.⁶ ............. C07D 239/36; C07D 403/10; C07D 413/14; A61K 31/505
[52] U.S. Cl. ............. 514/183; 514/210; 514/212; 514/227.8; 514/235.8; 514/269; 514/274; 540/481; 540/601; 544/60; 544/123; 544/310; 544/313; 544/319

[58] Field of Search ............... 514/210, 212, 514/183, 269, 274, 227.8, 235.8; 540/601, 481; 544/310, 313, 319, 60, 123

[56] References Cited

FOREIGN PATENT DOCUMENTS

| | | |
|---|---|---|
| 0 407 342 A2 | 1/1991 | European Pat. Off. . |
| 0 411 766 A1 | 2/1991 | European Pat. Off. . |
| 0 445 811 A2 | 9/1991 | European Pat. Off. . |
| WO 92/14468 | 9/1992 | WIPO . |
| WO 93/03018 | 2/1993 | WIPO . |
| WO 93/15717 | 8/1993 | WIPO . |

OTHER PUBLICATIONS

Chemical Abstracts, vol. 117, No. 25, 21 Dec. 1992 (Columbus, Ohio, USA), p. 694, col. 2, abstract No. 251363z, Shidara, Naganori et al., "Preparation of pyrimidine derivatives as angiotensin II receptor antagonists".

*Primary Examiner*—Mukund J. Shah
*Assistant Examiner*—Deepak Rao
*Attorney, Agent, or Firm*—Jacobson, Price, Holman & Stern, PLLC

[57] ABSTRACT

The invention relates to pyrimidinone derivatives and the pharmaceutically acceptable salts thereof having remarkable antagonistic action against angiotensin II receptor, and thus useful in treating cardiovascular diseases caused by angiotensin II.

10 Claims, No Drawings

PYRIMIDINONE DERIVATIVES

This application is a 371 of PCT/KR95/00121 filed Sep. 25, 1995.

BACKGROUND OF THE INVENTION

This invention relates to novel pyrimidinone derivatives and the pharmaceutically acceptable salts thereof. This invention also relates to process for preparing of the novel pyrimidinone derivatives and pharmaceutical composition containing the pyrimidinone derivatives.

The compounds of this invention and the pharmaceutically acceptable salts thereof are useful as angiotensin II antagonists especially, in treatment of various cardiovascular diseases caused by angiotensin II.

Renin-angiotensin system plays a central role in the regulation of blood pressure in human body. Angiotensin II, consisting of eight amino acids, is produced during the cleavage of angiotensin I by angiotensin converting enzyme (ACE) localized on the arterial blood vessels of lung, etc., and then involved in hypertension development. Angiotensin II, the final product of Renin-angiotensin system, exerts its action to elevate blood pressure and increase electrolyte concentration by interacting with specific receptors present in blood vessel, smooth muscle, kidney or adrenal gland. Thus, as a way of controlling hypertension several antagonistic compounds have been explored to inhibit the effect of angiotensin II by blocking its receptors.

Peptide antagonists analogous to angiotensin II are known, but their clinical applications have been limited because of their short half-life, extensive inactivation after oral administration and above all the partial agonistic activity.

Recently, several non-peptide compounds have been reported as angiotensin II antagonists. European Patent Application Laying-Open Publication Nos. 028,834 and 253310 disclose Imidazole derivatives substituted by biphenyl (for example, Losartan) and European Patent Application Laying-Open Publication No. 245,637, imidazopyridine derivatives (for example, L158,809) as potent angiotensin II antagonists.

In European Patent Application Laying-Open Publication Nos. 407,342, 419,048 and 445,811, pyrimidinone compounds similar to the compounds of this invention in their 6 membered heterocyclic ring structure are disclosed inclusively as a general formula without illustrative enough to support it. Further, the compounds described therein show relatively low activities($10^{-6}$ mol for 60~70% inhibition in in vitro blood vessel dilation study) than imidazole derivatives known in the above mentioned application.

DESCRIPTION OF THE INVENTION

In search of novel pyrimidinone compounds having at least 100 times more enhanced activities than the pyrimidinones disclosed in the prior art, the inventors of this invention have manufactured extensive pyrimidinones substituted by variety of functional groups and then investigated their angiotensin II antagonist activity.

The object of the invention, therefore, is to provide with novel pyrimidinone derivatives and the pharmaceutically acceptable salts thereof which inhibit the action of angiotensin II effectively.

Other object of the invention is to provide with process for preparing novel pyrimidinone derivatives and the pharmaceutically acceptable salts thereof which inhibit the action of angiotensin II effectively.

Another object of the invention is to provide with a pharmaceutical composition for treating hypertension including the novel pyrimidinone derivatives and the pharmaceutically acceptable salts thereof which inhibit the action of angiotensin II effectively.

In order to achieve the aforementioned objects, the present invention provides with pyrimidinone derivatives having the general formula (I):

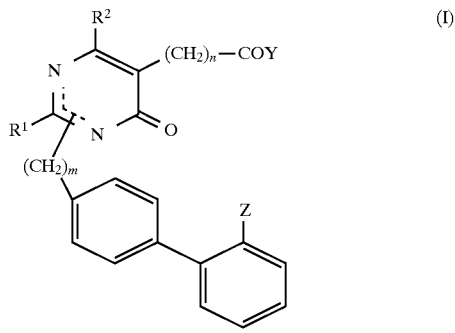

wherein:
$R^1$ is $C_1$~$C_4$ alkyl, cycloalkyl, $C_1$~$C_4$ alkoxy or $C_1$~$C_4$ alkylmercapto;
$R^2$ is H, halogen, $C_1$~$C_4$ alkyl, aryl or arylalkyl;
Y is $OR^3$, $SR^3$ or $NR^3R^4$;
$R^3$, $R^4$ is same or different H, cycloalkyl, aryl, arylalkyl, $C_1$~$C_4$ alkyl being optionally substituted by H, halogen, hydroxy, $C_1$~$C_4$ alkoxy, amino, alkylamino, dialkylamino(each alkyl having $C_1$~$C_5$), $C_1$~$C_4$ alkoxycarbonyl, carboxy or substituted aminocarbonyl, or $C_1$~$C_4$ alkyl or aryl carbonyl, $C_1$~$C_4$ alkoxy carbonyl or substituted aminocarbonyl; or
$R^3$ and $R^4$ are together with N atom forming 4 to 8 membered heterocyclic ring, which can be further substituted with one or two substituents selected from the group consisting of cycloalkyl, aryl, arylalkyl, $C_1$~$C_4$ alkyl being optionally substituted by H, halogen, hydroxy, $C_1$~$C_4$ alkoxy, amino, alkylamino, dialkylamino(each alkyl having $C_1$~$C_5$), $C_1$~$C_4$ alkoxycarbonyl, carboxy or substituted aminocarbonyl, and halogen, hydroxy, $C_1$~$C_4$ alkoxy, amino, alkylamino, dialkylamino(each alkyl having $C_1$~$C_5$), $C_1$~$C_4$ alkoxycarbonyl, carboxy and substituted aminocarbonyl; and the heterocyclic ring can further include —O—, —S—, —$SO_2$—, >N—$R^5$;
$R^5$ is H, $C_1$~$C_4$ alkyl, aryl, arylalkyl, substituted alkenyl, pyridyl, pyrimidyl, $C_1$~$C_4$ alkyl or arylcarbonyl, $C_1$~C4 alkoxy carbonyl, or substituted aminocarbonyl;
Z is CN, $COOR^3$ or tetrazol-5-yl radical having general formula

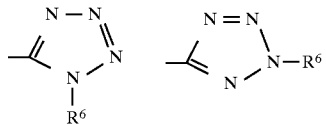

wherein
$R^6$ is H, t-butyl or triphenaylmethyl;
m is 1 or 2;
n is 1, 2, 3, 4, 5 or 6;
and the pharmaceutically acceptable salts thereof.

Pyrimidinone compounds according to the invention and pharmaceutically acceptable salts thereof exhibit remarkable antagonistic actions against angiotensin II receptors.

Preferable are such compounds of formula (I) wherein $R^1$ is ethyl, n-propyl, n-butyl, cyclopropyl, etoxy or propoxy; $R^2$ is H, halogen or $C_1 \sim C_4$ alkyl; Y is $OR^3$, $SR^3$ wherein $R^3$ is H, methyl, ethyl, propyl or butyl, or $NR^3R^4$ wherein $R^3$, $R^4$ are same or different H, methyl, ethyl, propyl or butyl, or $R^3$ and $R^4$ are together with N atom forming 4 to 8 membered cyclic ring, which can be further substituted with one or two substituents selected from the group consisting of cycloalkyl, aryl, arylalkyl, $C_1 \sim C_4$ alkyl being optionally substituted by H, halogen, hydroxy, $C_1 \sim C_4$ alkoxy, amino, alkylamino, dialkylamino(each alkyl having $C_1 \sim C_5$), $C_1 \sim C_4$ alkoxycarbonyl, carboxy or substituted aminocarbonyl, and halogen, hydroxy, $C_1 \sim C_4$ alkoxy, amino, alkylamino, dialkylamono(each alkyl having $C_1 \sim C_5$), $C_1 \sim C_4$ alkoxycarbonyl, carboxy and substituted aminocarbonyl, and the heterocyclic ring can further include —O—, —S—, —$SO_2$—, >N-$R^5$, wherein $R^5$ is H, $C_1 \sim C_4$ alkyl, aryl, arylalkyl, substituted alkenyl, pyridyl, pyrimidyl, $C_1 \sim C_4$ alkyl or arylcarbonyl, $C_1 \sim C_4$ alkoxy carbonyl, or substituted aminocarbonyl and the pharmaceutically acceptable salts thereof.

According to the invention, it has been found that the whole antagonistic activity of the pyrimidinone derivatives of formula (I) is closely associated with Y of the 5-position of the pyrimidinone ring. Y is preferably $OR^3$ or $NR^3R^4$, particularly $NR^3R^4$ as like amine, heteroamine or substituted amine wherein $R^3$ and $R^4$ are forming 4 to 8 membered cyclic ring together with the N atom to which they are attached.

Pharmaceutically acceptable salts of the invention include inorganic salts obtainable by reacting corresponding pyrimidinone compounds (I) with hydroxides of alkali or alkaline earth metals such as sodium hydroxide, potassium hydroxide, calcium hydroxide or magnesium hydroxide, carbonate of alkali or alkaline earth metals such as sodium carbonate, potassium carbonate, calcium carbonate or magnesium carbonate, or alcoholate of alkali or alkaline earth metals such as natrium, kalium or magnesium, and organic salts obtainable by reacting with organic amine in $H_2O$, lower alcohols such as methanol, ethanol, isopropyl alcohol, t-butyl alcohol, etc., tetrahydrofuran, or the mixture thereof.

The invention also provides with the process for preparing pyrimidinone derivatives of formula (I).

The compound of formula (I) can be prepared according to the following reaction steps;

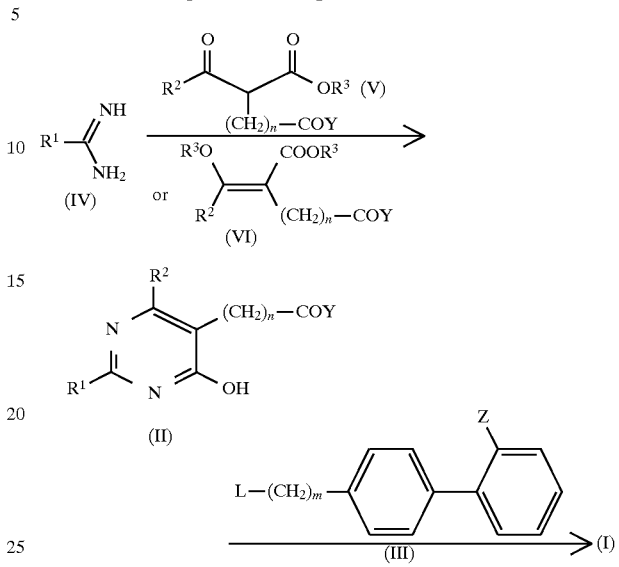

wherein $R^1$, $R^2$, $R^3$, Y, Z, m and n have the meaning defined in the above formula (I); L is halogen, alkyl or arylsulfonyloxy, or other conventional leaving groups.

The compound (I) can be prepared by reacting compound (II) with biphenyl compound (III) in the solution of dimethyl formamide or tetrahydrofuran containing 1 or 2 moles of NaH or alcoholate of alkali metal. Pyrimidinone compound of formula (II) is obtainable by condensing amidine compound (IV) with compound (V) or (VI) in the alcohol solution with reflux.

The compound of formula (I) wherein Z is tetrazol-5-yl and COY is carboxy, ester or amide can be prepared as follows:

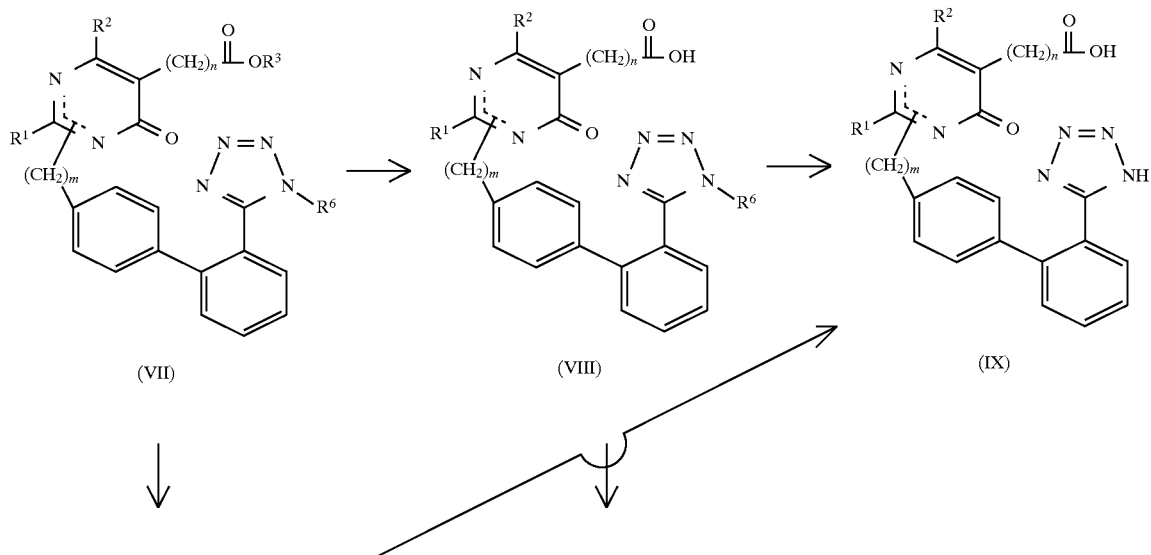

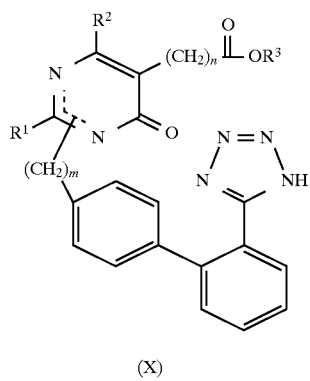

(X)

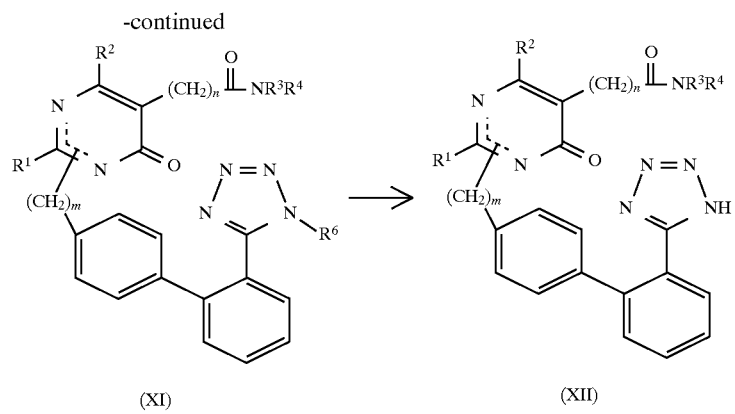

(XI) (XII)

wherein $R^1$, $R^2$, $R^3$, $R^4$, $R^6$, m and n have the meaning defined in the above formula (I).

1) The compound (X) can be prepared by reacting compound (VII) with 0.5~6N hydrochloric acid or trifluoroacetic acid in the solution of methanol, ethanol or tetrahydrofuran.

2) The compound (IX) can be prepared from compound (VIII) employing the procedure for preparation of compound (X) from compound (VII). The compound (VIII) is obtainable through hydrolysis of compound (VII) by adding 1 to 5 moles of base such as sodium hydroxide or potassium hydroxide to the latter in the solution of methanol, ethanol or tetrahydrofuran containing $H_2O$. Alternatively, compound (IX) can be prepared from compound (X) using the procedure for preparation of compound (VIII) from compound (VII).

3) The compound (XII) can be prepared by in dimethyl formamide adding an appropriate amine, N-hydroxybenzotriazol, N-methylmorpholine and 1-(3-dimethylaminopropyl)-3-ethyl carbodiimide to compound (VIII) and thereby obtaining compound(XI); and then adding 0.5~6N hydrochloric acid or trifluoracetic acid to the resultant compound (XI) in the solution-of methanol, ethanol or tetrahyderfuran.

The compound of formula (I) wherein Z is carboxy radical and COY is carboxy or ester radical can be prepared as follows:

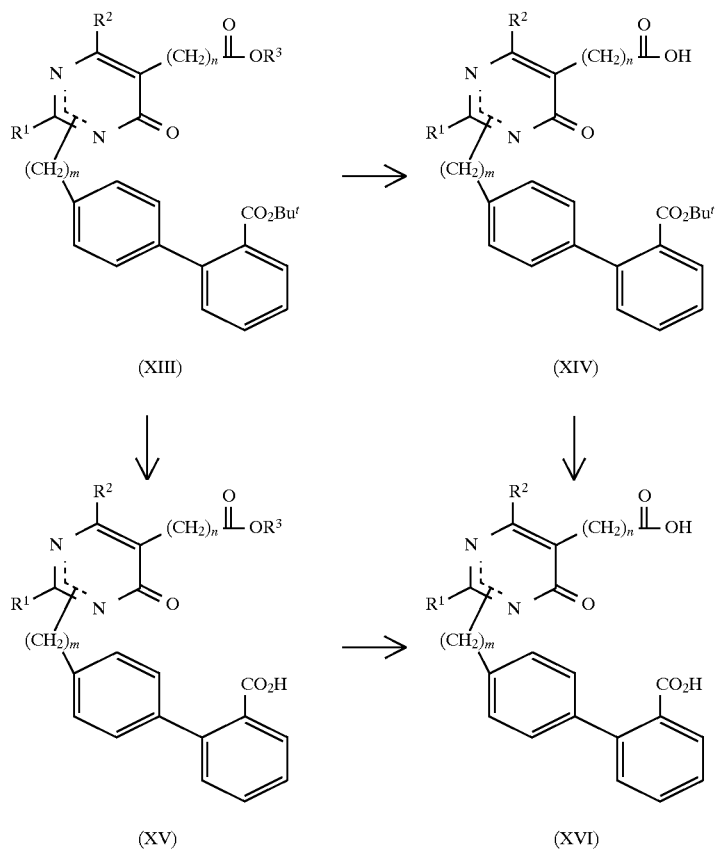

wherein $R^1$, $R^2$, $R^3$, m and n have the meaning defined in the above formula (I).

1) The compound (XV) can be prepared by reacting compound (XIII) with trifluoracetic acid in the solution of dichloromethane or tetrahydrofuran.

2) The compound (XVI) is obtainable through hydrolysis of compound (XV) by adding 2 to 5 moles of base such as sodium hydroxide or potassium hydroxide to the latter in the solution of methanol, ethanol or tetrahydrofuran which contains $H_2O$. Alternatively, compound (XVI) can be prepared by converting compound (XIII) to (XIV) using the procedure for preparation of compound (XVI) from compound (XV) and then adding trifluoracetic acid to the compound (XIV) in the solution of dichloromethane or tetrahydrofuran.

The compound (I) of the invention and the pharmaceutically acceptable salts thereof exert remarkable antagonistic effect on angiotensin II receptor.

Representative compounds of the invention are as follows:

2-ethyl-5-ethoxycarbonylmethyl-6-methyl-3-[[2'-(1H-tetrazol-5-yl)biphenyl-4-yl]methyl]-pyrimidin-4-(3H)-one (Compound 1)

2-ethyl-5-carboxymethyl-6-methyl-3-[[2'-(1H-tetrazol-5-yl)-biphenyl-4-yl]methyl]-pyrimidin-4-(3H)-one (Compound 2)

2-ethyl-5-carboxymethyl-6-methyl-1-[[2'-(1H-tetrazol-5-yl)-biphenyl-4-yl]methyl]-pyrimidin-4-(1H)-one (Compound 3)

2-ethyl-5-diethylaminocarbonylmethyl-6-methyl-3-[[2'-(1H-tetrazol-5-yl)biphenyl-4-yl]methyl]-pyrimidin-4-(3H)-one (Compound 4)

2-ethyl-5-(2'-ethoxycarbonylethyl)-6-methyl-3-[[2'-(1H-tetrazol-5-yl)biphenyl-4-yl]methyl]-pyrimidin-4-(3H)-one (Compound 5)

2-ethyl-5-(2'-carboxyethyl)-6-methyl-3-[[2'-(1H-tetrazol-5-yl)-biphenyl-4-yl]methyl]-pyrimidin-4-(3H)-one (Compound 6)

2-ethyl-5-(2'-carboxyethyl)-6-methyl-1-[[2'-(1H-tetrazol-5-yl)-biphenyl-4-yl]methyl]-pyrimidin-4-(1H)-one (Compound 7)

2-ethyl-5-(2'-diethylaminocarbonylethyl)-6-methyl-3-[[2'-(1 H-tetrazol-5-yl)biphenyl-4-yl]methyl]-pyrimidin-4 (3H)-one (Compound 8)

2-n-propyl-5-ethoxycarbonylmethyl-6-methyl-3-[[2'-(1H-tetrazol-5-yl)biphenyl-4-yl]methyl]-pyrimidin-4-(3H)-one (Compound 9)

2-n-propyl-5-carboxymethyl-6-methyl-3-[[2'-(1H-tetrazol-5-yl)-biphenyl-4-yl]methyl]-pyrimidin-4-(3H)-one (Compound 10)

2-n-propyl-5-carboxymethyl-6-methyl-1-[[2'-(1H-tetrazol-5-yl)-biphenyl-4-yl]methyl]-pyrimidin-4-(1H)-one (Compound 11)

2-n-propyl-5-diethylaminocarbonylmethyl-6-methyl-3-[[2'-(1H-tetrazol-5-yl)biphenyl-4-yl]methyl]-pyrimidin-4-(3H)-one (Compound 12)

2-n-propyl-5-(2'-ethoxyarbonylethyl)-6-methyl-3-[[2'-(1H-tetrazol-5-yl)biphenyl-4-yl]methyl]-pyrimidin -4-(3H)-one (Compound 13)

2-n-propyl-5-(2'-carboxyethyl)-6-methyl-3-[[2'-(1H-tetrazol-5-yl)-biphenyl-4-yl]methyl]-pyrimidin-4-(3H)-one (Compound 14)

2-n-propyl-5-($2'$-carboxyethyl)-6-methyl-1-[[2'-(1H-tetrazol-5-yl)-biphenyl-4-yl]methyl]-pyrimidin-4-(1H)-one (Compound 15)

2-n-propyl -5-(2'-diethylaminocarbonylethyl)-6-methyl-3-[[2'-(1H-tetrazol-5-yl)biphenyl-4-yl]methyl]-pyrimidin-4-(3H)-one (Compound 16)

2-n-butyl-5-ethoxycarbonylmethyl-6-methyl-3-[[2'-(1H-tetrazol-5-yl)biphenyl-4-yl]methyl]-pyrimidin-4-(3H)-one (Compound 17)

2-n-butyl-5-ethoxycarbonylmethyl-6-methyl-1-[[2'-(1H-tetrazol-5-yl)biphenyl-4-yl]methyl]-pyrimidin-4-(1H)-one (Compound 18)

2-n-butyl-5-carboxymethyl-6-methyl-3-[[2'-(1H-tetrazol-5-yl)-biphenyl-4-yl]methyl]-pyrimidin-4-(3H)-one (Compound 19)

2-n-butyl-5-carboxymethyl-6-methyl-1-[[2'-(1H-tetrazol-5-yl)-biphenyl-4-yl]methyl]-pyrimidin-4-(1H)-one (Compound 20)

2-n-butyl-5-diethylaminocarbonylmethyl-6-methyl-3-[[2'-(1H-tetrazol-5-yl)biphenyl-4-yl]methyl]-pyrimidin-4-(3H)-one (Compound 21)

2-n-butyl-5-dimethylaminocarbonylmethyl-6-methyl-3-[[2'-(1H-tetrazol-5-yl)biphenyl-4-yl]methyl]-pyrimidin-4-(3H)-one (Compound 22)

2-n-butyl-5-(2'-ethoxycarbonylethyl) -6-methyl -3-[[2'-(1H-tetrazol-5-yl)biphenyl-4-yl]methyl]-pyrimidin-4-(3H)-one (Compound 23)

2-n-butyl-5-(2'-ethoxycarbonylethyl)-6-methyl-1-[[2'-(1H-tetrazol-5-yl)biphenyl-4-yl]methyl]-pyrimidin-4-(1H)-one (Compound 24)

2-n-butyl-5-(2'-carboxyethyl)-6-methyl-3-[[2'-(1H-tetrazol-5-yl)-biphenyl-4-yl]methyl]-pyrimidin-4-(3H)-one (Compound 25)

2-n-butyl-5-(2'-carboxyethyl)-6-methyl-1-[[2'-(1H-tetrazol-5-yl)-biphenyl-4-yl]methyl]-pyrimidin-4-(1H)-one (Compound 26)

2-n-butyl-5-(2'-diethylaminocarbonylethyl)-6-methyl-3-[[2'-(1H-tetrazol -5-yl)biphenyl-4-yl]methyl]-pyrimidin -4-(3H )-one (Compound 27)

2-n-butyl-5-(2'-benzylaminocarbonylethyl)-6-methyl-3-[[2'-(1H-tetrazol-5-yl)biphenyl-4-yl]methyl]-pyrimidin -4-(3H)-one (Compound 28)

2-n-butyl-5-(3'-ethoxycarbonylpropyl)-6-methyl-3-[[2'-(1H-tetrazol-5-yl)biphenyl-4-yl]methyl]-pyrimidin-4-(3H)-one (Compound 29)

2-n-butyl-5-(3'-carboxypropyl)-6-methyl-3-[[2'-(1H-tetrazol -5-yl)biphenyl-4-yl]methyl]-pyrimidin-4-(3H)-one (Compound 30)

2-n-butyl-5-(3'-carboxypropyl)-6-methyl-1-[[2'-(1H-tetrazol-5-yl)biphenyl-4-yl]methyl]-pyrimidin-4-(1H)-one (Compound 31)

2-n-butyl-5-(3'-diethylaminocarbonylpropyl)-6-methyl-3-[[2'-(1H-tetrazol-5-yl)biphenyl-4-yl]methyl]-pyrimidin-4-(3H )-one (Compound 32)

2-n-butyl-5-(2'-ethoxycarbonylethyl)-6-ethyl-3-[[2'-(H-tetrazol-5-yl)biphenyl-4-yl]methyl]-pyrimidin-4-(3H)-one (Compound 33)

2-n-butyl-5-(2'-carboxyethyl)-6-ethyl-3-[[2'-(1H-tetrazol-5-yl)-biphenyl-4-yl]methyl]-pyrimidin-4-(3H)-one (Compound 34)

2-n-butyl-5-(2'-carboxyethyl)-6-ethyl-1-[[2'-(1H-tetrazol-5-yl)-biphenyl-4-yl]methyl]-pyrimidin-4-(1H)-one (Compound 35)

2-n-butyl-5-(2'-ethoxycarbonylethyl)-6-propyl-3-[[2'-(1 H-tetrazol-5-yl)biphenyl-4-yl]methyl]-pyrimidin-4-(3H)-one (Compound 36)

2-n-butyl-5-(2'-carboxyethyl)-6-propyl-1-[[2'-(1H-tetrazol-5-yl)-biphenyl-4-yl]methyl]-pyrimidin-4-(1H)-one (Compound 37)

2-n-butyl-5-ethoxycarbonylmethyl-6-methyl-3-(2'-carboxy-biphenyl-4-yl)methyl-pyrimidin-4-(3H)-one (Compound 38)

2-n-butyl-5-carboxymethyl-6-methyl-3-(2'-carboxybiphenyl-4-yl)methyl-pyrimidin-4-(3H)-one (Compound 39)

2-n-butyl-5-pyrrolidinocarbonylmethyl-6-methyl-3-[[2'-(1H-tetrazol-5-yl)biphenyl-4-yl]methyl]-pyrimidin-4-(3H)-one (Compound 40)

2-n-butyl-5-pyrrolidinocarbonylmethyl-6-methyl-1-[[2'-(1H-tetrazol-5-yl)biphenyl-4-yl]methyl]-pyrimidin-4-(1H)-one (Compound 41)

2-n-butyl-5-[(S)-2'-methoxycarbonylpyrrolidinocarbonylmethyl]-6-methyl-3-[[2'-(1H-tetrazol-5-yl)biphenyl-4-yl]methyl]-pyrimidin-4-(3H)-one (Compound 42)

2-n-butyl-5-[(S)-2'-aminocarbonylpyrrolidinocarbonylmethyl]-6-methyl-3-[[2'-(1H-tetrazol-5-yl)biphenyl-4-yl]methyl]-pyrimidin-4-(3H)-one (Compound 43)

2-n-butyl-5-(3'-pyrrolinocarbonylmethyl)-6-methyl-3-[[2'-(1H-tetrazol-5-yl)biphenyl-4-yl]methyl]-pyrimidin-4-(3H)-one (Compound 44)

2-n-butyl-5-piperidinocarbonylmethyl-6-methyl-3-[[2'-(1H-tetrazol-5-yl)biphenyl-4-yl]methyl]-pyrimidin-4-(3H)-one (Compound 45)

2-n-butyl-5-piperidinocarbonylmethyl-6-methyl-1-[[2'-(1H-tetrazol-5-yl)biphenyl-4-yl]methyl]-pyrimidin-4-(1H)-one (Compound 46)

2-n-butyl-5-(4'-benzylpiperidinocarbonylmethyl)-6-methyl-3-[[2'-(1H-tetrazol-5-yl)biphenyl-4-yl]methyl]-pyrimidin-4-(3H)-one (Compound 47)

2-n-butyl-5-(4'-methylpiperidinocarbonylmethyl)-6-methyl-3-[[2'-(1H-tetrazol-5-yl)biphenyl-4-yl]methyl]-pyrimidin-4-(3H)-one (Compound 48)

2-n-butyl-5-(3',3'-dimethylpiperidinocarbonylmethyl)-6-methyl-3-[[2'-(1H-tetrazol-5-yl)biphenyl-4-yl]methyl]-pyrimidin-4-(3H)-one (Compound 49)

2-n-butyl-5-(cis-2',6'-dimethylpiperidinocarbonylmethyl)-6-methyl-3-[[2'-(1H-tetrazol-5-yl)biphenyl-4-yl]methyl]-pyrimidin-4-(3H)-one (Compound 50)

2-n-butyl-5-(4'-ethoxycarbonylpiperidinocarbonylmethyl)-6-methyl-3-[[2'-(1H-tetrazol-5-yl)biphenyl-4-yl]methyl]-pyrimidin-4-(3H)-one (Compound 51)

2-n-butyl-5-(3'-ethoxycarbonylpiperidinocarbonylmethyl)-6-methyl-3-[[2'-(1H-tetrazol-5-yl)biphenyl-4-yl]methyl]-pyrimidin-4-(3H)-one (Compound 52)

2-n-butyl-5-(2'-ethoxycarbonylpiperidinocarbonylmethyl)-6-methyl-3-[[2'-(1H-tetrazol-5-yl)biphenyl-4-yl]methyl]-pyrimidin-4-(3H)-one (Compound 53)

2-n-butyl-5-(4'-aminocarbonylpiperidinocarbonylmethyl)-6-methyl-3-[[2'-(1H-tetrazol-5-yl)biphenyl-4-yl]methyl]-pyrimidin-4-(3H)-one (compound 54)

2-n-butyl-5-(3'-diethylaminocarbonylpiperidinocarbonylmethyl)-6-methyl-3-[[2'-(1H-tetrazol-5-yl)biphenyl-4-yl]methyl]-pyrimidin-4-(3H)-one (Compound 55)

2-n-butyl-5-hexamethyleneiminocarbonylmethyl-6-methyl-3-[[2'-(1H-tetrazol-5-yl)biphenyl-4-yl]methyl]-pyrimidin-4-(3H)-one (Compound 56)

2-n-butyl-5-heptamethyleneiminocarbonylmethyl-6-methyl-3-[[2'-(1H-tetrazol-5-yl)biphenyl-4-yl]methyl]-pyrimidin-4-(3H)-one (Compound 57)

2-n-butyl-5-(2'-pyrrolidinocarbonylethyl)-6-methyl-3-[[2'-(1H-tetrazol-5-yl)biphenyl-4-yl]methyl]-pyrimidin-4-(3H)-one (Compound 58)

2-n-butyl-5-[2'-((S)-2"-methoxycarbonylpyrrolidino)-carbonylethyl]-6-methyl-3-[[2'-(1H-tetrazol-5-yl)biphenyl-4-yl]-methyl]-pyrimidin-4-(3H)-one (Compound 59)

2-n-butyl-5-[2'-((S)-2"-aminocarbonylpyrrolidino)carbonylethyl]-6-methyl-3-[[2'-(1H-tetrazol-5-yl)biphenyl-4-yl]methyl]-pyrimidin-4-(3H)-one (Compound 60)

2-n-butyl-5-[2'-(3"-pyrrolino)carbonylethyl]-6-methyl-3-[[2'-(1H-tetrazol-5-yl)biphenyl-4-yl]methyl]-pyrimidin-4-(3H)-one (Compound 61)

2-n-butyl-5-[2'-piperidinocarbonylethyl]-6-methyl-3-[[2'-(1H-tetrazol-5-yl)biphenyl-4-yl]methyl]-pyrimidin-4-(3H)-one (Compound 62)

2-n-butyl-5-[2'-(4"-benzylpiperidino)carbonylethyl]-6-methyl-3-[[2'-(1H-tetrazol-5-yl)biphenyl-4-yl]methyl]-pyrimidin-4-(3H)-one (Compound 63)

2-n-butyl-5-[2'-(4"-methylpiperidino)carbonylethyl]-6-methyl-3-[[2'-(1H-tetrazol-5-yl)biphenyl-4-yl]methyl]-pyrimidin-4-(3H)-one (Compound 64)

2-n-butyl-5-[2'-(3",3"-dimethylpiperidino)carbonylethyl]-6-methyl-3-[[2'-(1H-tetrazol-5-ylbiphenyl-4-yl]methyl]-pyrimidin-4-(3H)-one (Compound 65)

2-n-butyl-5-[2'-(4"-ethoxycarbonylpiperidino)carbonylethyl]-6-methyl-3-[[2'-(1H-tetrazol-5-yl)biphenyl-4-yl]methyl]-pyrimidin-4-(3H)-one (Compound 66)

2-n-butyl-5-[2'-(2"-ethoxycarbonylpiperidino)carbonylethyl]-6-methyl-3-[[2'-(1H-tetrazol-5-yl)biphenyl-4-yl]methyl]-pyrimidin-4-(3H)-one (Compound 67)

2-n-butyl-5-[2'-(4"-aminocarbonylpiperidino)carbonylethyl]-6-methyl-3-[[2'-(1H-tetrazol-5-yl)biphenyl-4-yl]methyl]-pyrimidin-4-(3H)-one (Compound 68)

2-n-butyl-5-[2'-(3"-diethylaminocarbonylpiperidino)carbonylethyl]-6-methyl-3-[[2'-(1H-tetrazol-5-yl)biphenyl-4-yl]methyl]-pyrimidin-4-(3H)-one (Compound 69)

2-n-butyl-5-(2'-hexamethyleneiminocarbonylethyl)-6-methyl-3-[[2'-(1H-tetrazol-5-yl)biphenyl-4-yl]methyl]-pyrimidin-4-(3H)-one (Compound 70)

2-n-butyl-5-(2'-heptamethyleneiminocarbonylethyl)-6-methyl-3-[[2'-(1H-tetrazol-5-yl)biphenyl-4-yl]methyl]-pyrimidin-4-(3H)-one (Compound 71)

2-n-butyl-5-thiazolidinocarbonylmethyl-6-methyl-3-[[2'-(1H-tetrazol-5-yl)biphenyl-4-yl]methyl]-pyrimidin-4-(3H)-one (Compound 72)

2-n-butyl-5-morpholinocarbonylmethyl-6-methyl-3-[[2'-(1H-tetrazol-5-yl)biphenyl-4-yl]methyl]-pyrimidin-4-(3H)-one (Compound 73)

2-n-butyl-5-(3',5'-dimethylmorpholinocarbonylmethyl)-6-methyl-3-[[2'-(1H-tetrazol-5-yl)biphenyl-4-yl]methyl]-pyrimidin-4-(3H)-one (Compound 74)

2-n-butyl-5-thiomorpholinocarbonylmethyl-6-methyl-3-[[2'-(1H-tetrazol-5-yl)biphenyl-4-yl]methyl]-pyrimidin-4-(3H)-one (Compound 75) 2-n-butyl-5-(4'-methylpiperazinocarbonylmethyl)-6-methyl-3-[[2'-(1H-tetrazol-5-yl)biphenyl-4-yl]methyl]-pyrimidin-4-(3H)-one (Compound 76) 2-n-butyl-5-(4'-acetylpiperazinocarbonylmethyl)-6-methyl-3-[[2'-(1H-tetrazol-5-yl)biphenyl-4-yl]methyl]-pyrimidin-4-(3H)-one (Compound 77)

2-n-butyl-5-(2'-morpholinocarbonylethyl)-6-methyl-3-[[2'-(1H-tetrazol-5-yl)biphenyl-4-yl]methyl]-pyrimidin-4-(3H)-one (Compound 78)

2-n-butyl-5-[2'-(3",5"-dimethylmorpholino)carbonylethyl]-6-methyl-3-[[2'-(1H-tetrazol-5-yl)biphenyl-4-yl]methyl]-pyrimidin-4-(3H)-one (Compound 79)

2-n-butyl-5-(2'-thiomorpholinocarbonylethyl)-6-methyl-3-[[2'-(1H-tetrazol-5-yl)biphenyl-4-yl]methyl]-pyrimidin-4-(3H)-one (Compound 80)

2-n-butyl-5-[2'-(4"-acetylpiperazino)carbonylethyl]-6-methyl-3-[[2'-(1H-tetrazol-5-yl)biphenyl-4-yl]methyl]-pyrimidin-4-(3H)-one (Compound 81)

2-n-butyl-5-[2'-(4"-(2'"-pyridyl)piperazino)carbonylethyl]-6-methyl-3-[2'-(1H-tetrazol-5-yl)biphenyl-4-yl]methyl]-pyrimidin-4-(3H)-one (Compound 82)

2-n-butyl-5-[2'-(4"-trans-cinnamylpiperazino)carbonylethyl]-6-methyl-3-[[2'-(1H-tetrazol-5-yl)biphenyl-4-yl]methyl]-pyrimidin-4-(3H)-one (Compound 83)

The following examples are provided to illustrate the preparation of the compound of formula (I) and their incorporation into pharmaceutical compositions and as such are not to be considered as limiting the scope of the present invention.

PREPARATION OF STARTING MATERIAL

PROPIOAMIDINE

After dissolving 150 g of propionitrile in 400 ml of ethanol, 100 g of HCl gas was added for 30 minutes at 0°. The mixture was stirred for 12 hours at room temperature and then excess HCl gas and ethanol were removed in vacuo. After adding 500 ml of ether and stirring, the solid substance thus produced were filtered and then washed with 300 ml of ether. The solid substance was dried under the reduced pressure, dissolved in 400 ml of ethanol and then $NH_3$ gas was added to the resulting solution for an hour at 0° C. The solution was filtered and the filtered solution was concentrated to half of the orginal volume. The solid substance thus obtained was filtered again and the filtered solution was concentrated under ther reduced pressure. The oily product was allowed to stand in frigerater for a day and night to obtain 70 g of propioamidine, 30% yield.

$^1$H NMR(DMSO-$d_6$): δ 1.23(t, 3H), 2.42(q, 2H), 9.15(brs, 3H)

BUTYROAMIDINE

Butyroamidine compound was prepared similarly to propioamidine except that 207 g of butyronitrile was used in place of 150 g of propionitrile, 30% yield (100 g).

$^1$H NMR(DMSO-$d_6$): δ 1.01(t, 3H), 1.68~1.74(m, 2H), 2.21(t, 2H), 8.33(brs, 3H)

VALERAMIDINE

Valeramidine was prepared similarly to propioamidine except that 300 g of valernitrile was used in place of 150 g of propionitrile, 30% yield (109 g).

$^1$H NMR(DMSO-$d_6$): δ 0.89(t, 3H), 1.20~1.40(m, 2H), 1.48~1.62(m, 2H), 2.29(t, 2H), 6.50(brs, 3H).

EXAMPLE 1

2-ethyl-5-ethoxycarbonylmethyl-4-hydroxy-6-metyl pyrimidine 3.26 g of propioamidine and 10.0 ml of diethyl acetyl succinate were dissolved in 100 ml of ethanol, and 2.40 g of sodium ethylate was added thereto. The solution was refluxed for 3 hours and then ethanol was evaporated under the reduced pressure. The resultant oil was neutralized with 2N HCl and extracted twice with ethyl acetate. The organic layer thus obtained was dried over anhydrous $MgSO_4$ and recrystallized with petroleum ether to give 1.5 g of the title compound, yield 22%.

IR(KBr)cm$^{-1}$: 1740, 1665, 1620. $^1$H NMR(DMSO-$d_6$): δ 1.32(t, 3H), 2.30(t, 3H), 2.72(q, 2H), 3.50(s, 2H), 4.18(q, 2H).

EXAMPLE 2

2-ethyl-5-ethoxycarbonylmethyl-6-methyl-3-[[2'-(N-triphenyl-methyltetrazol-5-yl)biphenyl-4-yl]methyl]-pyrimidin-4-(3H)-one [compound (A)]; and 2-ethyl-5-ethoxycarbonylmethyl-6-methyl-1-[[2'-(N-triphenyl-methyltetrazol-5-yl]biphenyl-4-yl]methyl]-pyrimidin-4-(1H)-one [compound (B)]

After 1.34 g of the compound obtained from Example 1 was dissolved in 15.0 ml of dimethylformamide, 216 mg of NaH was added slowly and then stirred for 30 minutes at room temperature. To the mixture 3.34 g of 4-[2'-(N-triphenylmethyl-tetrazol-5-yl)phenyl]benzyl bromide was added, stirred for 12 hours at room temperature and dimethylformamide was removed in vacuo. The residue was separated and purified on a silica-gel column using hexane-ethyl acetate(4:1) to give 1.30 g of the compound (A) [31% yield] and 1.20 g of the compound (B) [29% yield]

Compound (A)

IR(neat)cm$^{-1}$: 1740, 1665, 1600. $^1$H NMR(CDCl$_3$): δ 1.22~1.41(m, 6H), 2.51(s, 3H), 2.92(q, 2H), 3.23(s, 2H), 4.12(q, 2H), 5.4(s, 2H), 6.85~6.95(q, 7H), 7.12~7.62(m, 15H), 7.94(dd, 1H).

Compound (B)

IR(neat)cm$^{-1}$: 1735, 1620 $^1$H NMR(CDCl$_3$): δ 1.15(t, 3H), 2.51(s, 3H), 2.92(q, 2H), 3.61(s, 2H), 4.13(q, 2H), 5.45(s, 2H), 6.85~6.95(q, 7H), 7.15~7.55(m, 15H), 7.94(dd, 1H).

EXAMPLE 3

2-ethyl-5-ethoxycarbonylmethyl-6-methyl-3-[[2'-(1H-tetrazol-5-yl)biphenyl-4-yl]methyl]-pyrimidin-4-(3H)-one (compound 1)

After 200 mg of the compound (A) obtained in Example 2 was dissolved in 10.0 ml of tetrahydrofuran, 4N HCl solution was added dropwise slowly and then stirred for 2 hours at room temperature. The mixture was neutralized with 4N NaOH solution. The aqueous layer was saturated with solid sodium chloride and extracted three times with ethyl acetate.

The organic layer was washed with brine and dried over anhydrous $MgSO_4$. The residue was chromotographed using firstly chloroform and then chlorform/methanol(9:1) to give 30 mg of the compound 1, 23% yield.

M.P.: 77°~81° C.; IR(KBr)cm$^{-1}$: 1740, 1665, 1600. $^1$H NMR(CDCl$_3$): δ 1.11~1.29(m, 6H), 2.25(s, 3H), 2.67(q, 2H), 3.61(s, 2H), 4.08(q, 2H), 5.34(s, 2H), 7.12(s, 4H), 7.52~7.78(m, 4H).

EXAMPLE 4

2-ethyl-5-carboxymethyl-6-methyl-3-[[2'-(N-triphenyl methyl-tetrazol-5-yl)biphenyl-4-yl]methyl]-pyrimidin-4-(3H)-one After 500 mg of the compound (A) obtained in Example 2 was dissolved in the solution of methanoVtetrahydrofuran (3:1), 25 ml of 10% NaOH solution was added dropwise and the mixture was stirred for 6 hours at room temperature. The solution was concentrated under the reduced pressure, neutralized with 4N HCl and then extracted three times with ethyl acetate. The organic layer was washed with brine and dried over anhydrous $MgSO_4$. The residue was chromatographed using chloroform/methanol(9:1) to give 220 mg of the title compound, 40% yield.

IR(KBr)cm$^{-1}$: 1660, 1600. $^1$H NMR(CDCl$_3$): δ 1.15(t, 3H), 2.30(s, 3H), 2.80(q, 2H), 3.40(s, 2H), 5.42(s, 2H), 7.22(d, 5H), 7.24~7.41(m, 13H), 7.45~7.81(m, 4H), 7.85 (dd, 1H).

EXAMPLE 5

2-ethyl-5-carboxymethyl-6-methyl-3-[[2'-(1H-tetrazol-5-yl)-biphenyl-4-yl]methyl]-pyrimidin-4-(3H)-one (compound 2)

The title compound (70 mg) was prepared from 200 mg of the compound obtained in Example 4 using the procedure in Example 3, 54% yield.

M.P.: 325°~329° C.; IR(KBr)cm$^{-1}$: 1660, 1620. $^1$H NMR (CDCl$_3$): δ 1.12(t, 3H), 2.22(s, 3H), 2.75(q, 2H), 3.65(s, 2H), 5.73(s, 2H), 6.92~7.57(m, 8H).

EXAMPLE 6

2-ethyl-5-carboxymethyl-6-methyl-1-[[2'-(N-triphenyl methyl-tetrazol-5-yl)biphenyl-4-yl]methyl]-pyrimidin-4-(1H)-one After 1.2 g of the compound (B) obtained in Example 2 was dissolved in the solution of methanoVtetrahydrofuran (1:3), 25 ml of 10% NaOH solution was added dropwise and the mixture was stirred for 6 hours at room temperature. The solution was concentrated under the reduced pressure, neutralized with 4N HCl and then extracted three times with ethyl acetate. The organic layer was washed with brine and dried over anhydrous MgSO$_4$. The residue was chromatographed using chloroform/methanol(9:1) to give 600 mg of the title compound, 50% yield.

IR(KBr)cm$^{-1}$: 1720, 1575. $^1$H NMR(CDCl$_3$): δ 1.15(t, 3H), 2.45(q, 2H), 3.41(s, 2H), 5.42(s, 2H), 6.85(m, 3H), 7.15(dd, 2H), 7.24~7.78(m, 17H), 7.85(dd, 1H).

EXAMPLE 7

2-ethyl-5-carboxymethyl-6-methyl-1-[[2'-(1H-tetrazol-5-yl)-biphenyl-4-yl]-pyrimidin-4-(1H)-one (compound 3)

The title compound (200 mg) was prepared from 600 mg of the compound obtained in Example 6 using the procedure in Example 3, 52% yield.

M.P.: 317°~322 ° C.; IR(KBr)cm$^{-1}$: 1580. $^1$H NMR (CDCl$_3$): δ 1.24(t, 3H), 2.34(s, 3H), 2.70(q, 2H), 3.63(s, 2H), 5.46(s, 2H), 7.12~7.61(m, 8H).

EXAMPLE 8

2-ethyl-5-diethylaminocarbonylmethyl-6-methyl-3-[[2'-(N -triphenylmethyltetrazol-5-yl)b iphenyl-4-yl]methyl]-pyrimidin-4-(3H)-one The compound obtained in Example 4 (400 mg) was dissolved in 10 ml of dimethylformamide. To the solution, 0.14 ml of diethylamine, 180 mg of N-hydroxybezotriazole, 0.15 ml of N-methylmorpholine and 260 mg of 1-(3-dimethyl-aminopropyl)-3-ethylcarbodiimide were added stepwise and stirred for 5 hours at room temperature. 30 ml of saturated NaHCO$_3$ was added to the reaction mixture, and then extracted three times with ethyl acetate. The organic layer was washed twice with H$_2$O and once with brine, dried and concentrated under the reduced pressure. The residue was chromatographed using ethyl acetate/hexane(2:3) to give 250 mg of the title compound, 63% yield.

IR(neat)cm$^{-1}$: 1660, 1610. $^1$H NMR(CDCl$_3$): δ 1.11~1.31 (t, 9H), 1.33(s, 3H), 2.75(q, 2H), 3.31~3.55(m, 4H), 3.62(s, 2H), 6.85~6.98(m, 8H), 7.11(dd, 2H), 7.22~7.38(m, 10H), 7.48(m, 2H), 7.98(dd, 1H).

EXAMPLE 9

2-ethyl-5-diethylaminocarbonylmethyl-6-methyl-3-[[2'-(1H-tetrazol-5-yl)biphenyl-4-yl]methyl]-pyrimidin-4-(3H)-one (compound 4)

The title compound (40 mg) was prepared from 250 mg of the compound obtained in Example 8 using the procedure in Example 3, 15% yield.

M.P.: 125°~131° C.; IR(KBr)cm$^{-1}$: 1660, 1620, 1555. $^1$H NMR(CDCl$_3$): δ 1.15(t, 9H), 2.35(s, 3H), 2.42~2.83(m, 4H), 3.31~3.71(m, 4H), 5.28(s, 2H), 7.12(s, 4H), 7.41~7.78(m, 4H).

EXAMPLE 10

2-ethyl-5-(2'-ethoxycarbonylethyl)-4-hydroxy-6-methyl-pyrimidine

The title compound (1.99 g) was prepared from 5.00 g of propioamidine and 15.0 mg of diethyl 2-acetylglutarate using the procedure in Example 1, 18% yield.

IR(KBr)cm$^{-1}$: 1740, 1665, 1620. $^1$H NMR(DMSO-d$_6$): δ 1.52(m, 6H), 2.17(s, 3H), 2.25~2.35(m, 4H), 2.42(t, 2H).

EXAMPLE 11

2-ethyl-5-(2'-ethoxycarbonylethyl)-6-methyl-3-[[2'-(N-triphenyl-methyltetrazo-5-yl)biphenyl-4-yl] methyl]-pyrimidin-4-(3H)-one [compound (C)]; and 2-ethyl-5-(2'-ethoxycarbonylethyl)-6-methyl-1-[[2'-(N-triphenyl-methyltetrazol-5-yl)biphenyl-4-yl] methyl]-pyrimidin-4-(1H)-one [compound (D)]

The compound (C) (1.42 g: 28% yield) and the compound (D) (1.23 g: 24% yield) were prepared from 1.04 g of the compound obtained in Example 10, 20 ml of dimethylformamide, 210 mg of NaH and 3.32 g of 4-[2'-(N-triphenylmethyl-tetrazol-5-yl)phenyl]benzyl bromide using the procedure in Example 2.

Compound (C)
IR(neat)cm$^{-1}$: 1740, 1665, 1600. $^1$H NMR(CDCl$_3$): δ 1.11~1.32(m, 6H), 2.43(s, 3H), 2.45~2.72(m, 4H), 2.94(t, 2H), 4.15(q, 2H), 5.24(s, 2H), 6.85~7.62(m, 22H), 7.94(dd, 1H).

Compound (D)
IR(neat)cm$^{-1}$: 1735, 1620. $^1$H NMR(CDCl$_3$): δ 1.11~1.31 (m, 6H), 2.35(s, 3H), 2.42~2.74(m, 4H), 2.90(t, 2H), 4.15(q, 2H), 5.23(s, 2H), 6.85~6.98(m, 8H), 7.11(d, 2H), 7.21~7.41 (m, 10H), 7.55(m, 2H), 7.99(m, 1H).

EXAMPLE 12

2-ethyl-5-(2'-ethoxycarbonylethyl)-6-methyl-3-[[2'-(1H-tetrazol-5-yl)biphenyl-4-yl]methyl]-pyrimidin-4-(3H)-one (compound 5)

The title compound (35 mg) was prepared from 200 mg of the compound (C) obtained in Example 11 using the procedure in Example 3, 25% yield.

M.P.: 76°~80° C.; IR(KBr)cm−1: 1740, 1665, 1600. $^1$H NMR(CDCl$_3$): δ 1.11~1.32(m, 6H), 2.54(t, 5H), 2.87~3.08 (m, 4H), 4.13(q, 2H), 5.44(s, 2H), 6,97~7.66(m, 8H).

EXAMPLE 13

2-ethyl-5-(2'-carboxyethyl)-6-methyl-3-[[2'-(N-triphenyl-methyl-tetrazol-5-yl)biphenyl-4-yl]methyl]-pyrimidin-4-(3H)-one The title compound (200 mg) was prepared from 500 mg of the compound (C) obtained in Example 11 using the procedure in Example 4, 34% yield.

IR(KBr)cm$^{-1}$: 1660, 1600. $^1$H NMR(CDCl$_3$): δ 1.24(t, 3H), 2.42(s, 3H), 2.70(q, 2H), 3.43~3.65(m, 4H), 5.31(s, 2H), 6.87~6.92(m, 6H), 7.12(dd, 2H) 7.21~7.42(m, 11H), 7.45~7.70(m, 3H), 7.85(dd, 1H).

EXAMPLE 14

2-ethyl-5-(2'-carboxyethyl)-6-methyl-3-[[2'-(H-tetrazol-5-y)-biphenyl-4-yl]methyl]-pyrimidin-4-(3H)-one (compound 6)

The title compound (320 mg) was prepared from 700 mg of the compound obtained in Example 13 using the procedure in Example 3, 70% yield.

M.P.: 318°~321° C.; IR(KBr)cm$^{-1}$: 1660, 1620. $^1$H NMR (CDCl$_3$): δ 1.10(t, 3H), 2.21(s, 3H), 2.70(q, 2H), 3.31~3.72 (m, 4H), 5.21(s, 2H), 6.92~7.62(m, 8H).

EXAMPLE 15

2-ethyl-5-(2'-carboxyethyl)-6-methyl-1-[[2'-(N-triphenyl-methyl-tetrazol-5-yl)-biplhenyl-4-yl]methyl]-pyrimidin-4-(1 H)-one The title compound (600 mg) was prepared from 1.20 g of the compound (D) obtained in Example 11 using the procedure in Example 6, 40% yield.

IR(KBr)cm$^{-1}$: 1720, 1580. $^1$H NMR(CDCl$_3$): δ 1.11~1.38 (m, 5H), 2.20(s, 3H), 2.61(q, 2H), 3.41~3.61(m, 4H), 5.25(s, 2H), 6.85~6.97(m, 6H), 7.11(dd, 2H), 7.21~7.42(m, 11H), 7.45~7.78(m, 3H), 7.98(dd, 1H).

EXAMPLE 16

2-ethyl-5-(2'-carboxyethyl)-6-methyl-1-[[2'-(1H-tetrazol-5-yl)-biphenyl-4-yl]methyl]-pyrimidin-4-(1H)-one (compound 7)

The title compound (250 mg) was prepared from 600 mg of the compound obtained in Example 15 using the procedure in Example 3, 65% yield.

M.P.: 317°~322° C.; IR(KBr)cm$^{-1}$: 1580. $^1$H NMR (CDCl$_3$): δ 1.18(t, 3H), 2.38(s, 3H), 2.66(q, 2H), 3.41~3.65 (m, 4H), 5.33(s, 2H), 6.85~7.81(m, 8H).

EXAMPLE 17

2-ethyl-5-(2'-diethylaminocarbonylethyl)-6-methyl-3-[[2'-(N-triphenylmethyltetrazol-5-yl)biphenyl-4-yl]methyl]-pyrimidin-4-(3H)-one The title compound (400 mg) was prepared from 600 mg of the compound obtained in Example 13 using the procedure in Example 8, 71% yield. IR(neat)cm$^{-1}$: 1660, 1610. $^1$H NMR(CDCl$_3$): δ 1.11~1.32(m, 9H), 2.33(s, 3H), 2.51(q, 2H), 2.65~2.85(m, 4H), 5.21(s, 3H), 6.85(m, 6H), 7.11(dd, 2H), 7.21~7.43(m, 11H), 7.45~7.72(m, 3H), 7.85(dd, 1H).

EXAMPLE 18

2-ethyl-5-(2'-diethylaminocarbonylethyl)-6-methyl-3-[[2'-(1H-tetrazol-5-yl)biphenyl-4-yl]methyl]-pyrimidin-4-(3H)-one (compound 8)

The title compound (50 mg) was prepared from 400 mg of the compound obtained in Example 17 using the procedure in Example 3, 16% yield.

M.P.: 100°~105° C.; IR(KBr)cm$^{-1}$: 1660, 1620, 1555. $^1$H NMR(CDCl$_3$): δ 1.01~1.32(m, 9H), 2.23(s, 3H), 2.60(q, 2H), 3.31~3.72(m, 6H), 5.33(s, 2H), 7.11(s, 4H), 7.15~7.25 (m, 4H).

The following compounds in Examples 19 to 93 were prepared similarly using the procedures in Examples 1 to 18.

EXAMPLE 19

2-n-propyl-5-ethoxycarbonylmethyl-6-methyl-3-[[2'-(1H-tetrazol-5-yl)biphenyl-4-yl]methyl]-pyrimidin-4-(3H)-one (compound 9)

M.P.: 93°~96° C.; IR(KBr)cm$^{-1}$: 1740, 1665, 1600. $^1$H NMR(CDCl$_3$): δ 0.98(t, 3H), 1.22(t, 3H), 1.74(q, 2H), 2.31(s, 3H), 2.54(t, 2H), 3.61(s, 2H), 4.21(q, 2H), 5.21(s, 2H), 6.89~7.11(d, 2H), 7.13~7.25(d, 2H), 7.33~7.45(m, 3H), 7.64(dd, 1H).

EXAMPLE 20

2-n-propyl-5-carboxymethyl-6-methyl-3-[[2'-(1H-tetrazol-5-yl)-biphenyl-4-yl]methyl]-pyrimidin-4-(3H)-one (compound 10)

M.P.: 318°~323° C.; IR(KBr)cm$^{-1}$: 1660, 1620. $^1$H NMR (CDCl$_3$): δ 0.91(t, 3H), 1.81(q, 2H), 2.31(s, 3H), 2.68(t, 2H), 3.74(s, 2H), 5.32(s, 2H), 6.85~7.12(m, 4H), 7.32(m, 3H), 7.54(dd, 1H).

EXAMPLE 21

2-n-propyl-5-carboxymethyl-6-methyl-1-[[2'-(1H-tetrazol-5-yl)-biphenyl-4-yl]methyl]-pyrimidin-4-(1H)-one (compound 11)

M.P.: 324°~328° C.; IR(KBr)cm$^{-1}$: 1580. $^1$H NMR (CDCl$_3$): δ 0.83(t, 3H), 1.56(m, 2H), 2.17(s, 3H), 2.65(s, 2H), 3.62(s, 2H), 5.27(s, 2H), 6.85~7.14(q, 4H), 7.35(m, 4H), 7.58(dd, 1H).

EXAMPLE 22

2-n-propyl-5-diethylaminocarbonylmethyl-6-methyl-3-[[2'-(1H-tetrazol-5-yl)biphenyl-4-yl]methyl]-pyrimidin-4-(3H)-one (compound 12)

M.P.: 124°~130° C.; IR(KBr)cm$^{-1}$: 1660, 1620, 1555. $^1$H NMR(CDCl$_3$): δ 1.05~1.32(m, 9H), 2.35(s, 3H), 2.65~2.85 (m, 2H), 3.31~3.64(m, 6H), 3.81(s, 2H), 6.89~7.21(m, 4H), 7.32~7.57(m, 3H), 7.89(dd, 1H).

EXAMPLE 23

2-n-propyl-5-(2'-ethoxycarbonylethyl)-6-methyl-3-[[2'-(1H-tetrazol-5-yl)biphenyl-4-yl]methyl]-pyrimidin-4-(3H)-one (compound 13)

M.P.: 93°~95° C.; IR(KBr)cm$^{-1}$: 1740, 1665, 1600. $^1$H NMR(CDCl$_3$): δ 0.86(t, 3H), 1.24(t, 3H), 1.62(q, 3H), 2.34(s, 3H), 2.42~2.71(m, 4H), 4.13(q, 2H), 5.17(s, 2H), 7.09(s, 4H), 7.52~7.79(m, 4H).

EXAMPLE 24

2-n-propyl-5-(2'-carboxyethyl)-6-methyl-3-[[2'-(1H-tetrazol-5-yl)-biphenyl-4-yl]methyl]-pyrimidin-4-(3H)-one (compound 14)

M.P.: 310°~313° C.; IR(KBr)cm$^{-1}$: 1660, 1620. $^1$H NMR (CDCl$_3$): δ 0.89(t, 3H), 1.56~1.87(m, 2H), 2.35(s, 3H), 2.51~2.71(t, 4H), 5.27(s, 2H), 6.96(d, 2H), 7.09~7.46(m, 5H), 7.56(dd, 1H).

EXAMPLE 25

2-n-propyl-5-(2'-carboxyethyl)-6-methyl-1-[[2'-(1H-tetrazol-5-yl)-biphenyl-4-yl]methyl]-pyrimidin-4-(1H)-one (compound 15)

M.P.: 329°~333° C.; IR(KBr)cm$^{-1}$: 1580. $^1$H NMR (CDCl$_3$): δ 0.93(t, 3H), 1.65~1.89(q, 2H), 2.22(m, 2H), 2.40(s, 3H), 2.41~2.78(m, 4H), 5.41(s, 2H), 6.96(d, 2H), 7.09(d, 2H), 7.28~7.32(m, 4H), 7.56(dd, 1H).

EXAMPLE 26

2-n-propyl-5-(2'-diethylaminocarbonylethyl)-6-methyl-3-[[2'-(1H-tetrazol-5-yl)biphenyl-4-yl]methyl]-pyrimidin-4-(3H)-one (compound 16)

M.P.: 97°~103° C.; IR(KBr)cm$^{-1}$: 1660, 1620, 1555. $^1$H NMR(CDCl$_3$): δ 1.05~1.29(t,.9H), 2.33(s, 3H), 2.52(t, 2H), 2.78~2.97(m, 4H), 3.32~3.45(q, 6H), 5.31(s, 2H), 6.99~7.08 (m, 4H), 7.32~7.58(m, 3H), 7.74(d, 1H).

EXAMPLE 27

2-n-butyl-5-ethoxycarbonylmethyl-6-methyl-3-[[2'-(1H-tetrazol-5-yl)biphenyl-4-yl]methyl]-pyrimidin-4-(3H)-one (compound 17)

IR(KBr)cm$^{-1}$: 1740, 1665, 1600. $^1$H NMR(CDCl$_3$): δ 0.86(t, 3H), 1.19(t, 3H), 1.22~1.39(m, 2H), 1.50~1.72(m, 2H), 2.24(s, 3H), 2.60(t, 2H), 3.51(s, 2H), 4.08(q, 2H), 5.17(s, 2H), 6.85~7.05(m, 4H), 7.30~7.58(m, 3H), 7.80(d, 1H).

EXAMPLE 28

2-n-butyl-5-ethoxycarbonylmethyl-6-methyl-1-[[2'-(1H-tetrazol-5-yl)biphenyl-4-yl]methyl]-pyrimidin-4-(1H)-one (compound 18)

IR(KBr)cm$^{-1}$: 1740, 1620, 1590. $^1$H NMR(CDCl$_3$): δ 0.89(t, 3H), 1.18(t, 3H), 1.21~1.40(m, 2H), 1.60~1.80(m, 2H), 2.19(s, 3H), 2.60(t, 2H), 3.56(s, 2H), 4.09(q, 2H), 5.39(s, 2H). 6.96~7.10(m, 2H), 7.15~7.30(m, 2H), 7.40~7.60(m, 3H), 7.91(d, 1H).

EXAMPLE 29

2-n-butyl-5-carboxymethyl-6-methyl-3-[[2'-(H-tetrazol-5-yl)-biphenyl-4-yl]methyl]-pyrimidin-4-(3H)-one (compound 19)

M.P.: 299°~302° C.; IR(KBr)cm$^{-1}$: 1660, 1620. $^1$H NMR (CDCl$_3$): δ 0.83(t, 3H), 1.20~1.40(m, 2H), 1.50~1.65(m, 2H), 2.22(s, 3H), 2.63(t, 2H), 3.31(s, 2H), 5.27(s, 2H), 6.96(d, 2H), 7.09(d, 2H), 7.28~7.32(m, 4H), 7.56(dd, 1H).

EXAMPLE 30

2-n-butyl-5-carboxymethyl-6-methyl-1-[[2'-(1H-tetrazol-5-yl)-biphenyl-4-yl]methyl]-pyrimidin-4-(1H)-one (compound 20)

M.P.: 319°~323° C.; IR(KBr)cm$^{-1}$: 1580. $^1$H NMR (DMSO-d$_6$): δ 0.91(t, 3H), 1.25~1.39(m, 2H), 1.64~1.76(m, 2H), 2.34(s, 3H), 2.71(t, 2H), 3.38(s, 2H), 5.32(s, 2H), 7.10~7.15(m, 2H), 7.27~7.40(m, 5H), 7.57(dd, 1H).

EXAMPLE 31

2-n-butyl-5-diethylaminocarbonylmethyl-6-methyl-3-[[2'-(1H-tetrazol-5-yl)biphenyl-4-yl]methyl]-pyrimidin-4-(3H)-one (compound 21)

M.P.: 96°~99° C.; IR(KBr)cm$^{-1}$: 1660, 1620, 1555. $^1$H NMR(CDCl$_3$): δ 0.88(t, 3H), 1.05(t, 3H), 1.24(t, 3H), 1.25~1.45(m, 2H), 1.55~1.75(m, 2H), 2.23(s, 3H), 2.62(t, 2H), 3.32(q, 2H), 3.45(q, 2H), 5.11(s, 2H), 6.92~7.08(m, 4H), 7.32~7.58(m, 3H), 7.78(d, 1H).

EXAMPLE 32

2-n-butyl-5-dimethylaminocarbonylmethyl-6-methyl-3-[[2'-(1H-tetrazol-5-yl)biphenyl-4-yl]methyl]-pyrimidin-4-(3H)-one (compound 22)

M.P.: 83°~87° C.; IR(KBr)cm$^{-1}$: 1660, 1620, 1555. $^1$H NMR(CDCl$_3$): δ 0.87(t, 3H), 1.25~1.40(m, 2H), 1.55~1.75 (m, 2H), 2.20(s, 3H), 2.58(t, 2H), 2.87(s, 3H), 3.11(s, 3H), 3.56(s, 2H), 5.10(s, 2H), 6.85~7.00(m, 3H), 7.25~7.58(m, 4H), 7.73(d,1H).

EXAMPLE 33

2-n-butyl-5-(2'-ethoxycarbonylethyl)-6-methyl-3-[[2'-(1H-tetrazol-5-yl)biphenyl-4-yl]methyl]-pyrimidin-4-(3H)-one (compound 23)

IR(KBr)cm$^{-1}$: 1740, 1665, 1600. $^1$H NMR(CDCl$_3$): δ 0.89(t, 3H), 1.22(t, 3H), 1.25~1.45(m, 2H), 1.55~1.75(m, 2H), 2.30(s, 3H), 2.47(t, 2H), 2.61(t, 2H), 2.77(t, 2H), 4.09(q, 2H), 5.20(s, 2H), 6.92~7.12(m, 3H), 7.36~7.62(m, 4H), 7.87(d, 1H).

EXAMPLE 34

2-n-butyl-5-(2'-ethoxycarbonylethyl)-6-methyl-1-[[2'-(1H-tetrazol-5-yl)biphenyl-4-yl]methyl]-pyrimidin-4-(1H)-one (compound 24)

IR(KBr)cm$^{-1}$: 1740, 1620, 1590. $^1$H NMR(CDCl$_3$): δ 0.86(t, 3H), 1.18(t, 3H), 1.21~1.35(m, 2H), 1.55~1.72(m, 2H), 2.46(t, 2H), 2.57(t, 2H), 2.86(t, 2H), 4.06(q, 2H), 5.42(s, 2H), 7.04(d, 2H), 7.20~7.30(m, 2H), 7.40~7.60(m, 3H), 7.87(dd, 1H).

EXAMPLE 35

2-n-butyl-5-(2'-carboxyethyl)-6-methyl-3-[[2'-(1H-tetrazol-5-yl) biphenyl-4-yl]methyl]-pyrimidin-4-(3H)-one (compound 25)

M.P.: 219°~222° C.; IR(KBr)cm$^{-1}$: 1645, 1550. $^1$H NMR (DMSO-d$_6$): δ 0.83(t, 3H), 1.20~1.39(m, 2H), 1.47~1.66(m, 2H), 2.27(s, 3H), 2.37(t, 2H), 2.55~2.73(m, 4H), 5.25(s, 2H), 6.97(d, 2H), 7.10(d, 2H), 7.28~7.45(m, 3H), 7.58(dd, 1H).

EXAMPLE 36

2-n-butyl-5-(2'-carboxyethyl)-6-methyl-1-[[2'-(H-tetrazol-5-yl)-biphenyl-4-yl]methyl]-pyrimidin-4-(1H)-one (compound 26)

M.P.: 189°~190° C.; IR(KBr)cm$^{-1}$: 1580. $^1$H NMR (DMSO-d$_6$): δ 0.91(t, 3H), 1.23~1.43(m, 2H), 1.62~1.82(m, 2H), 2.31(t, 2H), 2.41(s, 3H), 2.65~2.85(m, 4H). 5.42(s, 2H), 7.11(d, 2H), 7.29(d, 2H), 7.35~7.48(m, 3H), 7.59(dd, 1H).

EXAMPLE 37

2-n-butyl-5-(2'-diethylaminocarbonylethyl)-6-methyl-3-[[2'-(1H-tetrazol-5-yl)biphenyl-4-yl]methyl]-pyrimidin-4-(3H)-one (compound 27)

M.P.: 72°~75° C.; IR(KBr)cm$^{-1}$: 1660, 1610, 1550. $^1$H NMR(CDCl$_3$): δ 0.89(t, 3H), 1.04(t, 3H), 1.13(t, 3H), 1.25~1.45(m, 2H), 1.55~1.75(m, 2H), 2.28(s, 3H), 2.47(t, 2H), 2.62(t, 2H), 2.76(t, 2H), 3.31(q, 2H), 5.21(s, 2H), 6.98~7.13(m, 4H), 7.35~7.62(m, 3H), 7.83(dd, 1H).

EXAMPLE 38

2-n-butyl-5-(2'-benzylaminocarbonylethyl)-6-methyl-3-[[2'-(1H-tetrazol-5-yl)biphenyl-4-yl]methyl]-pyrimidin-4-(3H)-one (compound 28)

M.P.: 107° C.; IR(KBr)cm$^{-1}$: 1650, 1545. $^1$H NMR (CDCl$_3$): δ 0.88(t, 3H), 1.20~1.42(m, 2H), 1.55~1.75(m, 2H), 2.27(t, 2H), 2.32(s, 2H), 2.59(t, 2H), 2.80(t, 2H), 4.30(d, 2H), 5.05(s, 2H), 6.79(d, 2H), 6.95(d, 2H), 7.00~7.20(m, 5H), 7.30~7.60(m, 3H), 7.85(d, 1H).

EXAMPLE 39

2-n-butyl-5-(3'-ethoxycarbonylpropyl)-6-methyl-3-[
[2'-(1H-tetrazol-5-yl)biphenyl-4-yl]methyl]-
pyrimidin-4-(3H)-one (compound 29)

IR(CHCl$_3$)cm$^{-1}$: 1740, 1665. $^1$H NMR(CDCl$_3$): δ 0.89(t, 3H), 1.23(t, 3H), 1.30~1.48(m, 2H), 1.58~1.80(m, 2H), 2.28(s, 3H), 2.30(t, 2H), 2.48(t, 2H), 2.63(t, 2H), 4.10(q, 2H), 5.19(s, 2H), 7.01(d, 2H), 7.09(d, 2H), 7.36~7.60(m, 3H), 7.90(dd, 1H).

EXAMPLE 40

2-n-butyl-5-(3'-carboxypropyl)-6-methyl-3-[[2'-(1H-
tetrazol-5-yl)biphenyl-4-yl]methyl]-pyrimidin-4-
(3H)-one (compound 30)

M.P.: 225°~227° C.; IR(KBr)cm$^{-1}$: 1650, 1580. $^1$H NMR (DMSO-d$_6$): δ 0.83(t, 3H), 1.18~1.35(m, 2H), 1.45~1.75(m, 4H), 2.17(t, 2H), 2.48(t, 2H), 2.61(t, 2H), 5.25(s, 2H), 6.96(d, 2H), 7.10(d, 2H), 7.26~7.45(m, 3H), 7.56(dd, 1H).

EXAMPLE 41

2-n-butyl-5-(3'-carboxypropyl)-6-methyl-1-[[2'-(1H-
tetrazol-5-yl)biphenyl-4-yl]methyl]-pyrimidin-4-
(1H)-one (compound 31)

M.P.: 88°~90° C.; IR(KBr)cm$^{-1}$: 1740, 1660, 1620. $^1$H NMR(CDCl$_3$): δ 0.92(t, 3H), 1.28~1.43(m, 2H), 1.65~1.85 (m, 4H), 2.25~2.35(m, 2H), 2.36(s, 3H), 2.50~2.60(m, 2H), 2.73(t, 2H), 5.34(s, 2H), 7.12~7.24(m, 2H), 7.38~7.65(m, 5H), 8.06(dd, 1H).

EXAMPLE 42

2-n-butyl-5-(3'-diethylaminocarbonylpropyl)-6-
methyl-3-[[2'-(1H-tetrazol-5-yl)biphenyl-4-yl]
methyl]-pyrimidin-4-(3H)-one (compound 32)

IR(KBr)cm$^{-1}$: 1660, 1610, 1550. $^1$H NMR(CDCl$_3$): δ 0.88(t, 3H), 1.03(t, 3H), 1.14(t, 3H), 1.25~1.42(m, 2H), 1.55 1.75(m, 4H), 2.26(s, 3H), 2.33(t, 2H), 2.48(t, 2H), 2.62(t, 2H), 3.20~3.38(m, 4H), 5.15(s, 2H), 6.95~7.13(m, 4H), 7.30~7.55(m, 3H), 7.79(dd, 1H).

EXAMPLE 43

2-n-butyl-5-(2'-ethoxycarbonylethyl)-6-ethyl-3-[[2'-
(1H-tetrazol-5-yl)biphenyl-4-yl]methyl]-pyrimidin-
4-(3H)-one (compound 33)

IR(CHCl$_3$)cm$^{-1}$: 1740, 1660. $^1$H NMR(CDCl$_3$): δ 0.89(t, 3H), 1.15~1.28(m, 6H), 1.28~1.45(m, 2H), 1.60~1.78(m, 2H), 2.45(t, 2H), 2.52~2.70(m, 4H), 2.77(t, 2H), 4.08(q, 2H), 5.18(s, 2H), 6.95~7.12(m, 4H), 7.35~7.60(m, 3H), 7.90(dd, 1H).

EXAMPLE 44

2-n-butyl-5-(2'-carboxyethyl)-6-ethyl-3-[[2'-(1H-
tetrazol-5-yl)-biphenyl-4-yl]methyl]-pyrimidin-4-
(3H)-one (compound 34)

M.P.: 210° C.; IR(KBr)cm$^{-1}$: 1645, 1550. $^1$H NMR (DMSO-d$_6$): δ 0.83(t, 3H), 1.16(t, 3H), 1.20~1.35(m, 2H), 1.50~1.65(m, 2H), 2.37(t, 2H), 2.52~2.75(m, 6H), 5.25(s, 2H), 6.98(d, 4H), 7.09(d, 4H), 7.57(dd, 1H).

EXAMPLE 45

2-n-butyl-5-(2'-carboxyethyl)-6-ethyl-1-[[2'-(1H-
tetrazol-5-yl)-biphenyl-4-yl]methyl]-pyrimidin-4-
(1H)-one (compound 35)

M.P.: 220° C.; IR(KBr)cm$^{-1}$: 1580. $^1$H NMR(DMSO-d$_6$): δ 0.91(t, 3H), 1.18(t, 3H), 1.28~1.40(m, 2H), 1.60~1.80(m, 2H), 2.15~2.30(m, 2H), 2.62~2.85(m, 6H), 5.40(s, 2H), 7.12(d, 2H), 7.20~7.45(m, 5H), 7.57(dd, 1H).

EXAMPLE 46

2-n-butyl-5-(2'-ethoxycarbonylethyl)-6-propyl-3-[
[2'-(1H-tetrazol-5-yl)biphenyl-4-yl]methyl]-
pyrimidin-4-(3H)-one (compound 36)

IR(CHCl$_3$)cm$^{-1}$: 1740, 1660, 1620. $^1$H NMR(CDCl$_3$): δ 0.90(t, 3H), 0.98(t, 3H), 1.22(t, 3H), 1.28~1.42(m, 2H), 1.55~1.70(m, 4H), 2.40~2.70(m, 6H), 2.79(t, 2H), 4.10(q, 2H), 5.20(s, 2H), 6.97~7.12(m, 4H). 7.35~7.60(m, 3H), 7.95(d, 1H).

EXAMPLE 47

2-n-butyl-5-(2'-carboxyethyl)-6-propyl-1-[[2'-(1H-
tetrazol-5-yl)-biphenyl-4-yl]methyl]-pyrimidin-4-
(1H)-one (compound 37)

M.P.: 89°~92° C.; IR(KBr)cm$^{-1}$: 1660, 1610, 1560. $^1$H NMR(DMSO-d$_6$): δ 0.88(t, 3H), 0.93(t, 3H), 1.20~1.42(m, 2H), 1.53~1.70(m, 4H), 2.37~2.55(m, 2H), 2.58~2.90(m, 6H), 5.44(s, 2H), 7.12(d, 2H), 7.42(d, 2H), 7.50~7.80(m, 4H).

EXAMPLE 48

2-n-butyl-5-ethoxycarbonylmethyl-6-methyl-3-(2'-
carboxy-biphenyl-4-yl)methyl-pyrimidin-4-(3H)-one
(compound 38)

M.P.: 154°~158° C.; IR(CHCl,)cm$^{-1}$: 1740, 1660. $^1$H NMR(CDCl$_3$): δ 0.87(t, 3H), 1.26(t, 3H), 1.35~1.42(m, 2H), 1.50~1.70(m, 2H), 2.32(s, 3H), 2.72(t, 2H), 3.61(s, 2H), 4.17(q, 2H), 5.34(s, 2H), 7.12~7.19(m, 2H), 7.20~7.35(m, 3H), 7.35~7.58(m, 2H), 7.94(dd, 1H).

EXAMPLE 49

2-n-butyl-5-carboxymethyl-6-methyl-3-(2'-
carboxybiphenyl-4-yl)methyl-pyrimidin-4-(3H)-one
(compound 39)

M.P.: 125°~129° C. (decomposition). IR(KBr)cm$^{-1}$: 1720, 1660. $^1$H NMR(DMSO-d$_6$): δ 0.83(t, 3H), 1.21~1.40 (m, 2H), 1.48~1.70(m, 2H), 2.23(s, 3H), 2.67(t, 2H), 3.49(s, 2H), 5.34(s, 2H), 7.12~7.20(m, 2H), 7.22~7.60(m, 5H), 7.71(dd, 1H).

EXAMPLE 50

2-n-butyl-5-pyrrolidinocarbonylmethyl-6-methyl-3-[
[2'-(1H-tetrazol-5-yl)biphenyl-4-yl]methyl]-
pyrimidin-4-(3H)-one (compound 40)

M.P.: 53°~55° C.; IR(KBr)cm$^{-1}$: 1660, 1620, 1555. $^1$H NMR(CDCl$_3$): δ 0.84(t, 3H), 1.20~1.40(m, 2H), 1.52~1.70 (m, 2H), 1.85~1.95(m, 2H), 1.95~2.05(m, 2H), 2.20(s, 3H), 2.57(t, 2H), 3.34(t, 2H), 3.55(t, 2H), 3.55(t,2H), 5.09(s, 2H), 6.85~7.00(m, 4H), 7.25~7.55(m, 4H), 7.70(d, 1H).

EXAMPLE 51

2-n-butyl-5-pyrrolidinocarbonylmethyl-6-methyl-1-[
[2'-(1H-tetrazol-5-yl)biphenyl-4-yl]methyl]-
pyrimidin-4-(1H)-one (compound 41)

M.P.: 98°~105° C.; IR(KBr)cm$^{-1}$: 1660, 1620, 1550. $^1$H NMR(CDCl$_3$): δ 0.89~0.97(t, 3H), 1.20~1.92(m, 10H), 2.28

(s, 3H), 2.65~2.72(t, 2H), 3.32~3.52(m, 8H), 5.43(s, 2H), 7.07~7.11(d, 2H), 7.23~7.65(m, 6H), 8.01~8.07(dd, 1H).

EXAMPLE 52

2-n-butyl-5-[(S)-2'-methoxycarbonylpyrrolidinocarbonyl-methyl]-6-methyl-3-[[2'-(1H-tetrazol-5-yl)biphenyl-4-yl]-methyl]-pyrimidin-4-(3H)-one (compound 42)

M.P.: 145°~147° C.; IR(KBr)cm$^{-1}$: 1740, 1660, 1620, 1555. $^1$H NMR(CDCl$_3$): δ 0.80~0.88(t, 3H), 1.27~1.38(m, 2H), 1.52~1.64(m, 2H), 1.88~2.07(m, 3H), 2.23(s, 3H), 2.53~2.60(t, 2H), 3.43~3.74(m, 8H), 4.35~4.44(m, 1H), 5.09(s, 2H), 6.91(s, 4H), 7.29~7.51(m, 4H), 7.70~7.75(dd, 1H).

EXAMPLE 53

2-n-butyl-5-[(S)-2'-aminocarbonylpyrrolidinocarbonylmethyl]-6-methyl-3-[[2'-(1H-tetrazol-5-yl)biphenyl-4-yl]methyl]-pyrimidin-4-(3H)-one (compound 43)

M.P.: 195°~201° C.; IR(KBr)cm$^{-1}$: 1660, 1620, 1555. $^1$H NMR(CDCl$_3$): δ 0.79~0.92(t, 3H), 1.25~1.37(m, 2H), 1.56~1.63(m, 2H), 1.68~2.06(m, 2H), 2.23(s, 3H), 2.56~2.61(t, 2H), 3.43~3.74(m, 6H), 4.32~4.47(t, 1H), 5.09(s, 2H), 6.91(m, 4H), 7.29~7.63(m, 4H), 7.70~7.74(dd, 1H).

EXAMPLE 54

2-n-butyl-5-(3'-pyrrolinocarbonylmethyl)-6-methyl-3-[[2'-(1H-tetrazol-5-yl)biphenyl-4-yl]methyl]-pyrimidin-4-(3H)-one (compound 44)

M.P.: 219°~218° C.; IR(KBr)cm$^{-1}$: 1660, 1620, 1550. $^1$H NMR(CDCl$_3$): δ 0.86~0.95(t, 3H), 1.36~1.42(m, 2H), 1.62~1.76(m, 2H), 2.28(s, 3H), 2.62~2.69(t, 2H), 3.52(t, 2H), 4.17(m, 2H), 4.41(m, 2H), 5.13(s, 2H), 5.83(m, 2H), 6.95~7.09(m, 4H), 7.26~7.59(m, 4H), 7.86~7.92(dd, 1H).

EXAMPLE 55

2-n-butyl-5-piperidinocarbonylmethyl-6-methyl-3-[[2'-(1H-tetrazol-5-yl)biphenyl-4-yl]methyl]-pyrimidin-4-(3H)-one(compound 45)

M.P.: 94°~298° C.; IR(KBr)cm$^{-1}$: 1660, 1620, 1555. $^1$H NMR(CDCl$_3$): δ 0.91(t, 3H), 1.35~1.55(m, 2H), 1.55~1.75(m, 8H), 2.28(s, 3H), 2.69(t, 2H), 3.45~3.56(m, 4H), 3.57(s, 2H), 5.15(s, 2H), 6.98~7.15(m, 4H), 7.35~7.42(m, 1H), 7.48~7.60(m, 2H), 7.92(dd, 1H).

EXAMPLE 56

2-n-butyl-5-piperidinocarbonylmethyl-6-methyl-1-[[2'-(1H-tetrazol-5-yl)biphenyl-4-yl]methyl]-pyrimidin-4-(3H)-one(compound 46)

M.P.: 80°~83° C.; IR(KBr)cm$^{-1}$: 1660, 1620, 1555. $^1$H NMR(CDCl$_3$): δ 0.89~0.97(t, 3H), 1.20~1.92(m, 8H), 2.31(s, 3H), 2.69~2.75(t, 2H), 3.45~3.52(m, 4H), 3.59(s, 2H), 5.45(s, 2H), 7.10~7.15(m, 2H), 7.27~7.65(m, 6H), 8.01~8.07(dd, 1H).

EXAMPLE 57

2-n-butyl-5-(4'-benzylpiperidinocarbonylmethyl)-6-methyl-3-[[2'-(1H-tetrazol-5-yl)biphenyl-4-yl]methyl]-pyrimidin-4-(3H)-one (compound 47)

M.P.: 119°~124° C.; IR(KBr)cm$^{-1}$: 1660, 1620, 1555. $^1$H NMR(CDCl$_3$): δ 0.86~0.94(t, 3H), 1.18~1.37(m, 4H), 1.65~1.82(m, 6H), 2.25(s, 3H), 2.52~2.69(m, 4H), 2.92~3.09(t, 1H), 3.57(s, 2H), 3.92~4.02(m, 1H), 4.42~4.53(m, 1H), 5.14(s, 2H), 6.95~7.39(m, 10H), 7.45~7.59(m, 2H), 7.87~7.89(dd, 1H).

EXAMPLE 58

2-n-butyl-5-(4'-methylpiperidinocarbonylmethyl)-6-methyl-3-[[2'-(1H-tetrazol-5-yl)biphenyl-4-yl]methyl]-pyrimidin-4-(3H)-one (compound 48)

M.P.: 109°~113° C.; IR(KBr)cm$^{-1}$: 1660, 1620, 1555. $^1$H NMR(CDCl$_3$): δ 0.81~0.96(t, 6H), 1.02~1.39(m, 3H), 1.51~1.78(m, 6H), 2.28(s, 3H), 2.64~2.73(t, 3H), 3.01~3.18(t, 1H), 3.59(t, 2H), 3.92~4.02(t, 1H), 4.45~4.52(m, 1H), 5.19(s, 2H), 7.07~7.15(m, 4H), 7.29~7.58(m, 4H), 7.95~8.01(dd, 1H).

EXAMPLE 59

2-n-butyl-5-(3',3'-dimethylpiperidinocarbonylmethyl)-6-methyl-3-[[2'-(1H-tetrazol-5-yl)biphenyl-4-yl]methyl]-pyrimidin-4-(3H)-one (compound 49)

M.P.: 123°~129° C.; IR(KBr)cm$^{-1}$: 1660, 1620, 1555. $^1$H NMR(CDCl$_3$): δ 0.86~0.99(m, 9H), 1.21~1.78(m, 8H), 2.25(s, 3H), 2.62~2.69(m, 2H), 3.20(s, 2H), 3.43~3.62(t, 4H), 5.19(s, 2H), 6.95~7.15(m, 4H), 7.35~7.59(m, 4H), 7.90~7.95(dd, 1H).

EXAMPLE 60

2-n-butyl-5-(cis-2',6'-dimethylpiperidinocarbonylmethyl)-6-methyl-3-[[2'-(1H-tetrazol-5-yl)biphenyl-4-yl]methyl]-pyrimidin-4-(3H)-one (compound 50)

M.P.: 89°~96° C.; IR(KBr)cm$^{-1}$: 1660, 1620, 1555. $^1$H NMR(CDCl$_3$): δ 0.82~2.04(m, 16H), 2.25(s, 3H), 2.57~2.71(t, 2H), 3.71(s, 2H), 4.27(m, 1H), 4.65(m, 1H), 5.23(s, 2H), 6.92~7.15(m, 4H), 7.34~7.62(m, 4H), 7.88~7.94(dd, 1H).

EXAMPLE 61

2-n-butyl-5-(4'-ethoxycarbonylpiperidinocarbonylmethyl)-6-methyl-3-[[2'-(1H-tetrazol-5-yl)biphenyl-4-yl]methyl]-pyrimidin-4-(3H)-one (compound 51)

M.P.: 109°~114° C.; IR(KBr)cm$^{-1}$: 1740, 1660, 1620, 1555. $^1$H NMR(CDCl$_3$): δ 0.82~0.90(t, 3H), 1.13~1.45(m, 5H), 1.58~1.87(m, 3H), 1.88~1.99(m, 2H), 2.28(s, 3H), 2.45~2.84(m, 4H), 3.33~3.44(t, 1H), 3.59(s, 2H), 3.95~4.17(m, 4H), 4.22~4.43(d, 1H), 5.19(s, 2H), 7.03~7.15(m, 4H), 7.28~7.62(m, 4H), 7.86~7.93(dd, 1H).

EXAMPLE 62

2-n-butyl-5-(3'-ethoxycarbonylpiperidinocarbonylmethyl)-6-methyl-3-[[2'-(1H-tetrazol-5-yl)biphenyl-4-yl]methyl]-pyrimidin-4-(3H)-one (compound 52)

M.P.: 134°~138° C.; IR(KBr)cm$^{-1}$: 1740, 1660, 1620, 1555. $^1$H NMR(CDCl$_3$): δ 0.86~0.94(t, 3H), 1.17~1.45(m, 6H), 1.60~2.14(m, 7H), 2.26(s, 3H), 2.28~2.68(m, 3H), 3.06~3.21(t, 1H), 3.42~3.69(m, 3H), 3.82~3.97(m, 2H), 4.01~4.19(m, 2H), 5.14(s, 2H), 6.927.08(m, 4H), 7.32~7.58(m, 4H), 7.86~7.98(dd, 1H).

EXAMPLE 63

2-n-butyl-5-(2'-ethoxycarbonylpiperidinocarbonylmethyl)-6-methyl-3-[[2'-(1H-tetrazol-5-yl)biphenyl-4-yl]methyl]-pyrimidin-4-(3H)-one (compound 53)

M.P.: 127°~131° C.; IR(KBr)cm$^{-1}$: 1660, 1620, 1555. $^1$H NMR(CDCl$_3$): δ 0.85~0.93(t, 3H), 1.18~1.39(m, 7H), 1.52~1.81(m, 4H), 1.81~2.05(m, 1H), 2.23(s, 3H), 2.58~2.64(t, 2H), 3.21~3.98(t, 5H), 4.10~4.25(m, 2H), 5.14 (s, 2H), 5.23(m, 1H), 6.96~7.08(m, 4H), 7.33~7.62(m, 4H), 7.84~7.91(dd, 1H).

EXAMPLE 64

2-n-butyl-5-(4'-aminocarbonylpiperidinocarbonylmethyl)-6-methyl-3-[[2'-(1H-tetrazol-5-yl)biphenyl-4-yl]methyl]-pyrimidin-4-(3H)-one (compound 54)

M.P.: 194°~198° C.; IR(KBr)cm$^{-1}$: 1660, 1620, 1555. $^1$H NMR(CDCl$_3$): δ 0.85~0.91(t, 3H), 1.18~1.38(m, 3H), 1.57~1.92(m, 8H), 2.35(s, 3H), 2.50~2.61(t, 2H), 3.64(s, 2H), 4.07~4.18(m, 1H), 4.48~4.$^6$1(m, 1H), 5.20(s, 2H), 5.23(m, 1H), 6.91~7.14(m, 4H), 7.31~7.67(m, 4H), 7.81~7.89(dd, 1H).

EXAMPLE 65

2-n-butyl-5-(3'-diethylaminocarbonylpiperidinocarbonyl-methyl)-6-methyl-3-[[2'-(1H-tetrazol-5-yl)biphenyl-4-yl]-methyl]-pyrimidin-4-(3H)-one (compound 55)

M.P.: 130°~134° C.; IR(KBr)cm$^{-1}$: 1660, 1620, 1555. $^1$H NMR(CDCl$_3$): δ 0.87~1.81(m, 18H), 2.17(s, 3H), 2.59~2.69 (m, 4H), 3.07~3.71(m, 8H), 4.45~4.58(m, 1H), 5.28(s, 2H), 7.04~7.09(m, 4H), 7.32~7.58(m, 4H), 7.84~7.91(dd, 1H).

EXAMPLE 66

2-n-butyl-5-hexamethyleneiminocarbonylmethyl-6-methyl3-[[2'-(1H-tetrazol-5-yl)biphenyl-4-yl]methyl]-pyrimidin-4-(3H)-one (compound 56)

M.P.: 125°~130° C.; IR(KBr)cm$^{-1}$: 1660, 1620, 1555. $^1$H NMR(CDCl$_3$): δ 0.84~0.89(t, 3H), 1.16~1.79(m, 12H), 2.24 (s, 3H), 2.58~2.65(t, 2H), 3.42~3.61(m, 6H), 5.13(s, 2H), 6.93~7.04(m, 4H), 7.33~7.57(m, 4H), 7.80~7.84(dd, 1H).

EXAMPLE 67

2-n-butyl-5-heptamethyleneiminocarbonylmethyl-6-methyl-3-[[2'-(1H-tetrazol-5-yl)biphenyl-4-yl]methyl]-pyrimidin-4-(3H)-one (compound 57)

M.P.: 121°~125° C.; IR(KBr)cm$^{-1}$: 1660, 1620, 1555. $^1$H NMR(CDCl$_3$): δ 0.85~0.92(t, 3H), 1.18~1.82(m, 14H), 2.23 (s, 3H), 2.58~2.67(t, 2H), 3.37~3.61(m, 6H), 5.11(s, 2H), 6.93~7.05(m, 4H), 7.31~7.81(m, 4H), 7.84~7.85(dd, 1H).

EXAMPLE 68

2-n-butyl-5-(2'-pyrrolidinocarbonylethyl)-6-methyl-3-[[2'-(1H-tetrazol-5-yl)biphenyl-4-yl]methyl]-pyrimidin-4-(3H)-one (compound 58)

M.P.: 228°~234° C.; IR(KBr)cm$^{-1}$: 1660, 1620, 1555. $^1$H NMR(CDCl$_3$): δ 0.85~0.88(t, 3H), 1.23~1.37(m, 2H), 1.41~1.68(m, 2H), 1.78~1.95(m, 4H), 2.28(s, 3H), 2.35~2.46(t, 2H), 2.46~2.60(t, 2H), 2.63~2.74(t, 2H), 5.22 (s, 2H), 7.04~7.13(m, 4H), 7.38~7.59(m, 4H), 7.89~7.92 (dd, 1H).

EXAMPLE 69

2-n-butyl-5-[2'-((S)-2"-methoxycarbonylpyrrolidino) carbonyl-ethyl]-6-methyl-3-[[2'-(1H-tetrazol-5-yl) biphenyl-4-yl]methyl]-pyrimidin-4-(3H)-one (compound 59)

M.P.: 147°~150° C.; IR(KBr)cm$^{-1}$: 1740, 1660, 1620, 1555. $^1$H NMR(CDCl$_3$): δ 0.82~0.92(t, 3H), 1.23~1.41(m, 2H), 1.60~1.68(m, 2H), 1.84~2.04(m, 3H), 2.30(s, 3H), 2.45~2.64(m, 4H), 2.76~2.83(t, 2H), 3.43~3.69(m, 6H), 4.37~4.42(m, 1H), 5.19(s, 2H), 6.91~7.03(m, 4H), 7.33~7.55(m, 4H), 7.82~7.88(dd, 1H).

EXAMPLE 70

2-n-butyl-5-[2'-((S)-2"-aminocarbonylpyrrolidino) carbonyl-ethyl]-6-methyl-3-[[2'-(1H-tetrazol-5-yl) biphenyl-4-yl]methyl]-pyrimidin-4-(3H)-one (compound 60)

M.P.: 213°~219° C.; IR(KBr)cm$^{-1}$: 1660, 1620, 1555. $^1$H NMR(CDCl$_3$): δ 0.72~0.92(t, 3H), 1.12~1.32(m, 2H), 1.47~1.61(m, 2H), 1.82~1.91(m, 2H), 2.31(s, 3H), 2.41~2.62(m, 4H), 2.81~2.92(t, 2H), 3.28~3.69(m, 4H), 4.49~4.54(m, 1H), 5.18(s, 2H), 6.81~7.15(m, 4H), 7.38~7.62(m, 4H), 7.72~7.78(dd, 1H).

EXAMPLE 71

2-n-butyl-5-[2'-(3"-pyrrolino)carbonylethyl]-6-methyl-3-[[2'-(1H-tetrazol-5-yl)biphenyl-4-yl] methyl]-pyrimidin-4-(3H)-one (compound 61)

M.P.: 176®~178° C.; IR(KBr)cm$^{-1}$: 1660, 1620, 1555. $^1$H NMR(CDCl$_3$): δ 0.82~0.89(t, 3H), 1.17~1.39(m, 2H), 1.47~1.71(m, 2H), 2.31(s, 3H), 2.48~2.62(m, 4H), 2.81~2.85(t, 2H), 4.08~4.19(dd, 4H), 5.19(s 2H), 5.74(s, 2H), 6.83~6.96(m, 4H), 7.26~7.51(m, 4H), 7.79~7.84(dd, 1H).

EXAMPLE 72

2-n-butyi-5-[2'-piperidinocarbonylethyl]-6-methyl-3-[[2'-(1H-tetrazol-5-yl)biphenyl-4-yl]methyl]-pyrimidin-4-(3H)-one (compound 62)

M.P.: 120°~127° C.; IR(KBr)cm$^{-1}$: 1660, 1620, 1555. $^1$H NMR(CDCl$_3$): δ 0.86~0.92(t, 3H), 1.17~1.69(m, 10H), 2.28 (s, 3H), 2.45~2.78(m, 6H), 3.39~3.50(m, 4H), 5.22(s, 2H), 7.09~7.13(m, 4H), 7.38~7.62(m, 4H), 7.91~7.95(dd, 1H).

EXAMPLE 73

2-n-butyl-5-[2'-(4"-benzylpiperidino)carbonylethyl]-6-methyl-3-[[2'-(1H-tetrazol-5-yl)biphenyl-4-yl] methyl]-pyrimidin-4-(3H)-one (compound 63)

M.P.: 125°~129° C.; IR(KBr)cm$^{-1}$: 1660, 1620, 1555. $^1$H NMR(CDCl$_3$): δ 0.86~0.94(t, 3H), 1.11~1.39(m, 4H), 1.52~1.82(m, 6H), 2.35(s, 3H), 2.36~2.63(m, 7H), 2.82~2.92(t, 2H), 3.91~4.02(m, 1H), 4.58~4.67(m, 1H), 5.19(s, 2H), 7.09~7.63(m, 13H), 7.94~8.02(dd, 1H).

EXAMPLE 74

2-n-butyl-5-[2'-(4"-methylpiperidino)carbonylethyl]-6-methyl-3-[[2'-(1H-tetrazol-5-yl)biphenyl-4-yl] methyl]-pyrimidin-4-(3H)-one (compound 64)

M.P.: 160°~165° C.; IR(KBr)cm$^{-1}$: 1660, 1620, 1555. $^1$H NMR(CDCl$_3$): δ 0.85~1.12(m, 6H), 1.15~1.40(m, 3H), 1.57~1.69(m, 6H), 2.29(s, 3H), 2.42~2.81(m, 7H), 2.89~3.03(m, 1H), 3.81~3.93(m, 1H), 4.41~4.52(m, 1H), 5.22(s, 2H), 7.06~7.09(m, 4H), 7.41~7.59(m, 4H), 7.90~7.95(dd, 1H).

EXAMPLE 75

2-n-butyl-5-[2'-(3",3"-dimethylpiperidino) carbonylethyl]-6-methyl-3-[[2'-(1H-tetrazol-5-yl) biphenyl-4-yl]methyl]-pyrimidin-4-(3H)-one (compound 65)

M.P.: 124°~129° C.; IR(KBr)cm$^{-1}$: 1660, 1620, 1555. $^1$H NMR(CDCl$_3$): δ 0.88~0.95(m, 6H), 1.31~2.11(m, 11H), 2.31(s, 3H), 2.49~2.84(m, 4H), 3.09~3.21(m, 2H), 3.31~3.48(m, 2H), 3.95(m, 1H), 5.23(s, 2H), 7.09~7.13(m, 4H), 7.42~7.58(m, 4H), 7.91~8.02(dd, 1H).

EXAMPLE 76

2-n-butyl-5-[2'-(4"-ethoxycarbonylpiperidino) carbonylethyl]-6-methyl-3-[[2'-(1H-tetrazol-5-yl) biphenyl-4-yl]methyl]-pyrimidin-4-(3H)-one (compound 66)

M.P.: 129®~132° C.; IR(KBr)cm$^{-1}$: 1740, 1660, 1620, 1555. $^1$H NMR(CDCl$_3$): δ 0.84~0.88(t, 3H), 0.92 1.42(m, 5H), 1.53~1.71(m, 3H), 1.81~1.99(m, 2H), 2.31(s, 3H), 2.46~2.84(m, 8H), 3.02~3.15(t, 1H), 3.83~3.97(m, 2H), 4.05~4.16(m, 2H), 4.23~4.39(m, 1H), 5.21(s, 2H), 6.95~7.14(m, 4H), 7.37~7.67(m, 4H), 7.86~7.91(dd, 1H).

EXAMPLE 77

2-n-butyl-5-[2'-(2"-ethoxycarbonylpiperidino) carbonylethyl]-6-methyl-3-[[2'-(1H-tetrazol-5-yl) biphenyl-4-yl]methyl]-pyrimidin-4-(3H)-one (compound 67)

M.P.: 128°~134° C.; IR(KBr)cm$^{-1}$: 1740, 1660, 1620, 1555. $^1$H NMR(CDCl$_3$): δ 0.86~0.94(t, 3H), 1.20~1.44(m, 7H), 1.62~1.71(m, 4H), 1.81~2.17(m, 1H), 2.31(s, 3H), 2.55~2.79(m, 6H), 3.15~3.31(m, 1H), 3.81~3.98(t, 2H), 4.08~4.21(q, 2H), 5.23(s, 2H), 7.03~7.18(m, 4H), 7.36~7.61 (m, 4H), 7.93~8.01(dd, 1H).

EXAMPLE 78

2-n-butyl-5-[2'-(4"-aminocarbonylpiperidino) carbonylethyl]-6-methyl-3-[[2'-(1H-tetrazol-5-yl) biphenyl-4-yl]methyl]-pyrimidin-4-(3H)-one (compound 68)

M.P.: 240°~246° C.; IR(KBr)cm$^{-1}$: 1660, 1620, 1555. $^1$H NMR(CDCl$_3$): δ 0.78~0.86(t, 3H), 1.22 ~1.74(m, 11H), 2.37(s, 3H), 2.48~2.62(m, 4H), 2.81~2.98(t, 2H), 3.93~4.08 (m, 1H), 4.31~4.42(dd, 1H), 5.19(s, 2H), 6.78(s, 1H), 6.91~7.13(m, 4H), 7.28~7.61(m, 5H).

EXAMPLE 79

2-n-butyl-5-[2'-(3"-diethylaminocarbonylpiperidino) carbonyl-ethyl]-6-methyl-3-[[2'-(1H-tetrazol-5-yl) biphenyl-4-yl]methyl]-pyrimidin-4-(3H)-one (compound 69)

M.P.: 126°~129° C.; IR(KBr)cm$^{-1}$: 1660, 1620, 1555. $^1$H NMR(CDCl$_3$): δ 0.79~0.99(t, 3H), 1.10~1.29(m, 3H), 1.31~1.48(m, 2H), 1.63~1.78(m, 6H), 2.35(s, 3H), 2.41~2.72(m, 6H), 2.81~3.52(m, 6H), 3.84~3.91(m, 1H), 4.61~4.73(m, 1H), 5.19(s, 2H), 6.98~7.12(m, 4H), 7.42~7.61(m, 4H), 7.72~7.89(dd, 1H).

EXAMPLE 80

2-n-butyl-5-(2'-hexamethyleneiminocarbonylethyl)- 6-methyl-3-[[2'-(1H-tetrazol-5-yl)biphenyl-4-yl] methyl]-pyrimidin-4-(3H)-one (compound 70)

M.P.: 110°~116° C.; IR(KBr)cm$^{-1}$: 1660, 1620, 1555. $^1$H NMR(CDCl$_3$): δ 0.84~0.92(t, 3H), 1.17~1.73(m, 12H), 2.26 (s, 3H), 2.44~2.62(m, 4H), 2.71~2.79(t, 2H), 3.37~3.45(m, 4H), 5.19(s, 2H), 6.98~7.12(m, 4H), 7.32~7.57(m, 4H), 7.79~7.84(dd, 1H).

EXAMPLE 81

2-n-butyl-5-(2'-heptamethyleneiminocarbonylethyl)- 6-methyl-3-[[2'-(1H-tetrazol-5-yl)biphenyl-4-yl] methyl]-pyrimidin-4-(3H)-one (compound 71)

M.P.: 126°~130° C.; IR(KBr)cm$^{-1}$: 1660, 1620, 1555. $^1$H NMR(CDCl$_3$): δ 0.85~0.92(t, 3H), 1.23~1.65(m, 14H), 2.28 (s, 3H), 2.45~2.62(m, 4H), 2.72~2.78(t, 2H), 3.34~3.41(m, 4H), 5.21(s, 2H), 7.02~7.19(m, 4H), 7.32~7.57(m, 4H), 7.86~7.93(dd, 1H).

EXAMPLE 82

2-n-butyl-5-thiazolidinocarbonylmethyl-6-methyl-3- [[2'-(1H-tetrazol-5-yl)biphenyl-4-yl]methyl]- pyrimidin-4-(3H)-one (compound 72)

M.P.: 218°~224° C.; IR(KBr)cm$^{-1}$: 1660, 1620, 1555. $^1$H NMR(CDCl$_3$): δ 0.86~0.94(t, 3H), 1.31~1.39(m, 2H), 1.56~1.66(m, 2H), 2.31(s, 3H), 2.48~2.65(m, 4H), 2.71~2.76(t, 2H), 2.92~3.09(m, 2H), 3.68~3.78(m, 2H), 4.43~4.49(d, 2H), 5.22(s, 2H), 7.01~7.27(m, 4H), 7.36~7.59 (m, 4H), 7.87~7.94(dd, 1H).

EXAMPLE 83

2-n-butyl-5-morpholinocarbonylmethyl-6-methyl-3-[ [2'-(1H-tetrazol-5-yl)biphenyl-4-yl]methyl]- pyrimidin-4-(3H)-one (compound 73)

M.P.: 88°~92° C.; IR(KBr)cm$^{-1}$: 1660, 1620, 1555. $^1$H NMR(CDCl$_3$): δ 0.82(t, 3H), 1.15~1.38(m, 2H), 1.45~1.65 (m, 2H), 2.18(s, 3H), 2.60(t, 2H), 3.46(s, 2H), 3.59~3.62(m, 8H), 5.28(s, 2H), 7.08(s, 4H), 7.45~7.72(m, 4H).

EXAMPLE 84

2-n-butyl-5-(3',5'- dimethylmorpholinocarbonylmethyl)-6-methyl-3-[ [2'-(1H-tetrazol-5-yl)biphenyl-4-yl]methyl]- pyrimidin-4-(3H)-one (compound 74)

M.P.: 98°~104° C.; IR(KBr)cm$^{-1}$: 1660, 1620, 1555. $^1$H NMR(CDCl$_3$): δ 0.82~0.89(t, 3H), 1.22~1.41(m, 2H), 1.58~1.68(m, 2H), 2.35(s, 3H), 2.49~2.63(m, 6H), 3.62(s, 2H), 3.88~3.95(m, 4H), 5.17(s, 2H), 6.95~7.08(m, 4H), 7.26~7.68(m, 4H), 7.71~7.75(dd, 1H).

EXAMPLE 85

2-n-butyl-5-thiomorpholinocarbonylmethyl-6- methyl-3-[[2'-(1H-tetrazol-5-yl)biphenyl-4-yl] methyl]-pyrimidin-4-(3H)-one (compound 75)

M.P.: 139°~144° C.; IR(KBr)cm$^{-1}$: 1660, 1620, 1555. $^1$H NMR(CDCl$_3$): δ 0.80~0.84(t, 3H), 1.14~1.42(m, 8H), 1.52~1.59(m, 2H), 2.35(s, 3H), 2.47~2.56(t, 2H), 3.26~3.42 (m, 2H), 3.51~3.77(m, 4H), 3.98~4.15(m, 2H), 5.17(s, 2H), 6.89~7.08(m, 4H), 7.21~7.62(m, 4H), 7.82~7.92(dd, 1H).

EXAMPLE 86

2-n-butyl-5-(4'-methylpiperazinocarbonylmethyl)-6-methyl-3-[[2'-(1H-tetrazol-5-yl)biphenyl-4-yl]methyl]-pyrimidin-4-(3H)-one (compound 76)

M.P.: 166°~170° C.; IR(KBr)cm$^{-1}$: 1660, 1620, 1555. $^1$H NMR(DMSO-d$_6$): δ 0.88(t, 3H), 1.25~1.45(m, 2H), 1.55~1.75(m, 2H), 2.23(s, 3H), 2.42(s, 3H), 2.59~2.80(m, 6H), 3.60(s, 2H), 3.61~3.75(m, 4H), 5.25(s, 2H), 7.05~7.22 (m, 4H), 7.35~7.70(m, 4H).

EXAMPLE 87

2-n-butyl-5-(4'-acetylpiperazinocarbonylmethyl)-6-methyl-3-[[2'-(1H-tetrazol-5-yl)biphenyl-4-yl]methyl]-pyrimidin-4-(3H)-one (compound 77)

M.P.: 161°~166° C.; IR(KBr)cm$^{-1}$: 1660, 1620, 1555. $^1$H NMR(CDCl$_3$): δ 0.85~0.95(t, 3H), 1.31~1.45(m, 2H), 1.61~1.74(m, 2H), 1.99~2.07(m, 2H), 2.51(s, 3H), 2.61~2.72(m, 2H), 3.27~3.72(m, 10H), 5.21(s, 2H), 7.01~7.09(m, 4H), 7.39~7.61(m, 3H), 7.81~7.94(dd, 1H).

EXAMPLE 88

2-n-butyl-5-(2'-morpholinocarbonylethyl)-6-methyl-3-[[2'-(1H-tetrazol-5-yl)biphenyl-4-yl]methyl]-pyrimidin-4-(3H)-one (compound 78)

M.P.: 137°~142° C.; IR(KBr)cm$^{-1}$: 1660, 1620, 1555. $^1$H NMR(CDCl$_3$): δ 0.86~0.94(t, 3H), 1.32~1.45(m, 2H), 1.58~1.78(m, 2H), 2.31(s, 3H), 2.48~2.82(m, 6H), 4.43~4.61(m, 8H), 5.32(s, 2H), 7.07~7.15(m, 4H), 7.39~7.61(m, 4H), 7.95~7.99(dd, 1H).

EXAMPLE 89

2-n-butyl-5-[2'-(3",5"-dimethylmorpholino)carbonylethyl]-pyrimnidin-4-(3H)-one (compound 79)

M.P.:180°~185° C.; IR(KBr)cm$^{-1}$: 1660, 1620, 1555. $^1$H NMR(CDCl$_3$): δ 0.86~0.94(t, 3H), 1.13~1.32(m, 8H), 1.58~1.62(m, 2H), 2.36(s, 3H), 2.48~2.93(m, 8H), 3.44~3.53(m, 2H), 3.74~3.84(d, 1H), 4.41~4.48(d, 1H), 5.18(s, 2H), 6.90~7.08(m, 4H), 7.29~7.55(m, 4H), 7.81~7.88(dd, 1H).

EXAMPLE 90

2-n-butyl-5-(2'-thiomorpholinocarbonylethyl)-6-methyl-3-[[2'-(1H-tetrazol-5-yl)biphienyl-4-yl]methiyl]-pyrimidin-4-(3H)-one (compound 80)

M.P.: 186°~190° C.; IR(KBr)cm$^{-1}$: 1660, 1620, 1555. $^1$H NMR(CDCl$_3$): δ 0.82~0.93(t, 3H), 1.27~1.42(m, 2H), 1.52~1.64(m, 2H), 1.88~2.07(m, 3H), 2.23(s, 3H), 2.55~2.84(m, 10H), 3.74~3.89(m, 4H), 5.17(s, 2H), 6.91~7.06(m, 4H), 7.31~7.48(m, 4H), 7.77~7.82(dd, 1H).

EXAMPLE 91

2-n-butyl-5-[2'-(4"-acetylpiperazino)carbonylethyl]-6-methyl-3-[[2'-(1H-tetrazol-5-yl)biphenyl-4-yl]methyl]-pyrimidin-4-(3H)-one (compound 81)

M.P.: 144°~148° C.; IR(KBr)cm$^{-1}$: 1660, 1620, 1555. $^1$H NMR(CDCl$_3$): δ 0.85~0.93(t, 3H), 1.31~1.45(m, 2H), 1.61~1.74(m, 2H), 1.99~2.07(m, 3H), 2.35(s, 3H), 2.61~2.72(m, 4H), 2.72~3.59(m, 10H), 5.21(s, 2H), 7.01~7.09(m, 4H), 7.39~7.61(m, 4H), 7.81~7.94(dd, 1H).

EXAMPLE 92

2-n-butyl-5-[2'-(4"-(2'"-pyridyl)piperazino)carbonylethyl]-6-methyl-3-[[2'-(1H-tetrazol-5-yl)biphenyl-4-yl]methyl]-pyrimidin-4-(3H)-one (compound 82)

M.P.: 142°~147° C.; IR(KBr)cm$^{-1}$: 1660, 1620, 1555. $^1$H NMR(CDCl$_3$): δ 0.82~0.90(t, 3H), 1.25~1.42(m, 2H), 1.54~1.68(m, 2H), 2.29(s, 3H), 2.58~2.65(m, 4H), 2.83~3.23(d, 2H), 3.22~3.25(d, 2H), 3.33~3.53(m, 4H), 3.63~3.68(q, 2H), 5.19(s, 2H), 7.04~7.21(m, 4H), 7.41~7.59 (m, 4H), 7.78~7.92(dd, 1H).

EXAMPLE 93

2-n-butyl-5-[2'-(4"-trans-cinnamylpiperazino)carbonylethyl]-6-methyl-3-[[2'-(1H-tetrazol-5-yl)biphenyl-4-yl]methyl]-pyrimidin-4-(3H)-one (compound 83)

M.P.: 134°~139° C.; IR(KBr)cm$^{-1}$: 1660, 1620, 1555. $^1$H NMR(CDCl$_3$): δ 0.86~0.94(t, 3H), 1.29~1.43(m, 2H), 1.58~1.68(m, 2H), 2.45(s, 3H), 2.63~2.84(m, BH), 3.20~3.32(m, 4H), 3.61~3.67(m, 2H), 4.43~4.61(m, 8H), 5.17(s, 2H), 6.01~6.14(d, 1H), 6.46~6.54(d, 1H), 7.04~7.12 (m, 4H), 7.26~7.54(m, 9H), 7.79~7.84(dd, 1H).

EXPERIMENTAL TEST RESULTS

The antagonistic activity of the representative compounds of the invention was evaluated using the methodology describe below. The results are shown in Table 1.

From New Zealand White rabbits (male or female, 2~2.5 kg), aorta was isolated, and fat and connected tissue were removed therefrom. The aorta was cut into 3~4 mm to form ring samples. The aorta sample was suspended in 20 ml of organ bath (37° C.) containing modified Krebs-Henseleit solution saturated with 95% O$_2$/5% CO$_2$ (pH 7.4).

The aorta preparation was exposed consecutively to 2 g of tensile strength for 90 minutes intermittently washing the sample with 30 minutes interval and then to 30 mM of KCl to observe contraction response. After washing more than three times, the aorta preparation was again allowed to contract three times for stabilization by adding Angiotensin II (10 mM) thereto with 30 minutes interval. The third contraction response to Angiotensin II was considered as control.

10 minutes after the third contraction, the test compound was administered to the aorta preparation, which was incubated for 20 minutes.

Comparing angiotensin II contraction curve obtained from the above inhibition test with that of the control, IC$_{50}$ (concentration being required to inhibit angiotensin II induced contraction by 50%) was determined for each test compound(Table 1).

TABLE 1

| Compound No. | IC$_{50}$(nM) |
| --- | --- |
| Compound 1 | 9.05 |
| Compound 2 | 14.2 |
| Compound 3 | 22.3 |

TABLE 1-continued

| Compound No. | IC$_{50}$(nM) |
| --- | --- |
| Compound 4 | 15.1 |
| Compound 5 | 30.7 |
| Compound 6 | 22.7 |
| Compound 7 | 2.84 |
| Compound 8 | 73.6 |
| Compound 9 | 4.35 |
| Compound 10 | 37.1 |
| Compound 11 | 7.71 |
| Compound 12 | 5.59 |
| Compound 13 | 4.99 |
| Compound 14 | 7.39 |
| Compound 15 | 19.4 |
| Compound 16 | 174 |
| Compound 17 | 4.63 |
| Compound 18 | 93.3 |
| Compound 19 | 2.63 |
| Compound 20 | 8.53 |
| Compound 21 | 2.63 |
| Compound 22 | 2.37 |
| Compound 23 | 3.50 |
| Compound 24 | 169 |
| Compound 25 | 9.43 |
| Compound 26 | 42.8 |
| Compound 27 | 30.8 |
| Compound 28 | 92.3 |
| Compound 29 | 17.0 |
| Compound 30 | 7.26 |
| Compound 31 | 17.0 |
| Compound 32 | 2.95 |
| Compound 33 | 11.2 |
| Compound 34 | 4.17 |
| Compound 35 | 62.0 |
| Compound 36 | 44.5 |
| Compound 37 | 115 |
| Compound 38 | 335 |
| Compound 39 | 36.1 |
| Compound 40 | 2.74 |
| Compound 41 | 119 |
| Compound 42 | 2.06 |
| Compound 43 | 2.08 |
| Compound 44 | 2.04 |
| Compound 45 | 2.46 |
| Compound 46 | 405 |
| Compound 47 | 128 |
| Compound 48 | >10$^{-5}$(M) |
| Compound 49 | 8.96 |
| Compound 50 | 28.4 |
| Compound 51 | 5.99 |
| Compound 52 | 3.56 |
| Compound 53 | 6.24 |
| Compound 54 | 2.20 |
| Compound 55 | 3.64 |
| Compound 56 | 3.33 |
| Compound 57 | 3.60 |
| Compound 58 | 5.86 |
| Compound 59 | 3.36 |
| Compound 60 | 2.88 |
| Compound 61 | 7.85 |
| Compound 62 | 9.62 |
| Compound 63 | 302 |
| Compound 64 | >10$^{-5}$(M) |
| Compound 65 | 7.60 |
| Compound 66 | 9.70 |
| Compound 67 | 30.4 |
| Compound 68 | 2.29 |
| Compound 69 | 10.7 |
| Compound 70 | 11.6 |
| Compound 71 | 16.8 |
| Compound 72 | 9.13 |
| Compound 73 | 1.75 |
| Compound 74 | 1.03 |
| Compound 75 | 2.76 |
| Compound 76 | 3.59 |
| Compound 77 | 2.17 |
| Compound 78 | 5.22 |
| Compound 79 | 13.1 |
| Compound 80 | 4.06 |
| Compound 81 | 9.87 |
| Compound 82 | 53.0 |
| Compound 83 | 151 |

As shown in Table 1, the pyrimidinone compounds of the invention exhibit high efficacy of angiotensin II antagonistic action, demonstrating angiotensin II receptor inhibition at low concentration less than $10^{-8}$ mol.

Thus, the compound of the invention is useful in treating cardiovascular disease, especially in hypertension. Effective dose per day of the compound, 0.1 to 25 mg, preferably 5 to 15 mg may be administered to the patient once or twice a day.

The compound of the invention can be used in compositions such as tablets, capsules, etc. which can also contain pharmaceutically acceptable vehicle, excipient, binder, etc.

Illustrative of pharmaceutical compositions containing the compounds (I) of the invention as a active ingredient are the following.

EXAMPLE 94

TABLET

| COMPOSITION | WEIGHT (mg) |
| --- | --- |
| (1) Compound(40) | 15 |
| (2) Lactose | 45 |
| (3) Corn Starch | 110 |
| (4) Microcrystalline Cellulose | 25 |
| (5) Magnesium Stearate | 5 |
| | 200 |

The above ingredients (1) to (4) were mixed and granulated. To the granules magnesium stearate (5) was added, mixed and compressed to give a unit tablet (200 mg).

Similarly, tablets containing other compound of the invention were prepared. Each tablet can be administered to the patient once a day.

EXAMPLE 95

CAPSULE

| COMPOSITION | WEIGHT (mg) |
| --- | --- |
| (1) Compound(40) | 15 |
| (2) Lactose | 135 |
| (3) Microcrystalline Cellulose | 45 |
| (4) Magnesium Stearate | 5 |
| | 200 |

In a conventional way the ingredients were mixed, granulated and dispensed to give a unit capsule (200 mg).

Similarly, capsules containing other compound of the invention were prepared. Each capsule can be administered to the patient once a day.

We claim:
1. A compound of formula (I):

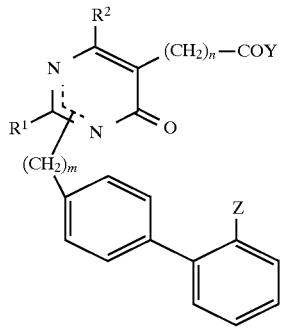

wherein:
$R^1$ is $C_1$~$C_4$ alkyl, cycloalkyl, $C_1$~$C_4$ alkoxy or $C_1$~$C_4$ alkylmercapto;
$R^2$ is H, halogen, $C_1$~$C_4$ alkyl, aryl or arylalkyl;
Y is $NR^3R^4$;
$R^3$, $R^4$ is same or different H, cycloalkyl, aryl, arylalkyl, $C_1$~$C_4$ alkyl being optionally substituted by H, halogen, hydroxy, $C_1$~$C_4$ alkoxy, amino, alkylamino, dialkylamino(each alkyl having $C_1$~$C_5$), $C_1$~$C_4$ alkoxycarbonyl, carboxy or substituted aminocarbonyl, or $C_1$~$C_4$ alkyl or aryl carbonyl, $C_1$~$C_4$ alkoxy carbonyl or substituted aminocarbonyl; or
$R^3$ and $R^4$ are together with N atom forming 4 to 8 membered heterocyclic ring, which can be further substituted with one or two substituents selected from the group consisting of cycloalkyl, aryl, arylalkyl, $C_1$~$C_4$ alkyl being optionally substituted by H, halogen, hydroxy, $C_1$~$C_4$ alkoxy, amino, alkylamino, dialkylamino(each alkyl having $C_1$~$C_5$), $C_1$~$C_4$ alkoxycarbonyl, carboxy or substituted aminocarbonyl, and halogen, hydroxy, $C_1$~$C_4$ alkoxy, amino, alkylamino, dialkylamino(each alkyl having $C_1$~$C_5$), $C_1$~$C_4$ alkoxycarbonyl, carboxy and substituted aminocarbonyl; and the heterocyclic ring can further include —O—, —S—, —$SO_2$—, >N—$R^5$;
$R^5$ is H, $C_1$~$C_4$ alkyl, aryl, arylalkyl, substituted alkenyl, pyridyl, pyrimidyl, $C_1$~$C_4$ alkyl or arylcarbonyl, $C_1$~$C_4$ alkoxy carbonyl, or substituted aminocarbonyl;
Z is CN, $COOR^3$ or tetrazol-5-yl radical having general formula

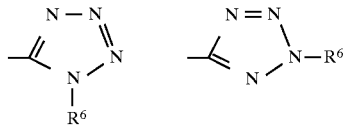

wherein
$R^6$ is H, t-butyl or triphenylmethyl;
m is 1 or 2;
n is 1, 2, 3, 4, 5 or 6;
and the pharmaceutically acceptable salts thereof.
2. The compound of claim 1 wherein:
$R^1$ is ethyl, n-propyl, n-butyl, cyclopropyl, ethoxy or propoxy;
$R^2$ is H, halogen or $C_1$~$C_4$ alkyl;
and the pharmaceutically acceptable salts thereof.
3. The compound of claim 1 wherein:
$R^3$ and $R^4$ are together with N atom forming 4 to 8 membered heterocyclic ring, which can be further substituted with one or two substituents selected from the group consisting of cycloalkyl, aryl, arylalkyl, $C_1$~$C_4$ alkyl being optionally substituted with H, halogen, hydroxy, $C_1$~$C_4$ alkoxy, amino, alkylamino, dialkylamino(each alkyl having $C_1$~$C_5$), $C_1$~$C_4$ alkoxycarbonyl, carboxy or substituted aminocarbonyl, and halogen, hydroxy, $C_1$~$C_4$ alkoxy, amino, alkylamino, dialkylamino(each alkyl having $C_1$~$C_5$), $C_1$~$C_4$ alkoxycarbonyl, carboxy and substituted aminocarbonyl; and
the pharmaceutically acceptable salts thereof.
4. The compound of claim 3 wherein:
said heterocyclic ring includes —O—, —S—, —$SO_2$—, >N—$R^5$, wherein $R^5$ is H, $C_1$~$C_4$ alkyl, aryl, arylalkyl, substituted alkenyl, pyridyl, pyrimidyl, $C_1$~$C_4$ alkyl or arylcarbonyl, $C_1$~$C_4$ alkoxy carbonyl, or substituted aminocarbonyl; and the pharmaceutically acceptable salts thereof.
5. The compound of claim 1 wherein said compound is the one selected from the group consisting of:
2-n-butyl-5-pyrrolidinocarbonylmethyl-6-methyl-3-[[2'-(1H-tetrazol-5-yl)biphenyl-4-yl]methyl]-pyrimidin-4-(3H)-one,
2-n-butyl-5-pyrrolidinocarbonylmethyl-6-methyl-1-[[2'-(1H-tetrazol-5-yl)biphenyl-4-yl]methyl]-pyrimidin-4-(1H)-one,
2-n-butyl-5-[(S)-2'-methoxycarbonylpyrrolidinocarbonylmethyl]-6-methyl-3-[[2'-(1H-tetrazol-5-yl)biphenyl-4-yl]methyl]-pyrimidin-4-(3H)-one,
2-n-butyl-5-[(S)-2'-aminocarbonylpyrrolidinocarbonylmethyl]-6-methyl-3-[[2'-(1H-tetrazol-5-yl)biphenyl-4-yl]methyl]-pyrimidin-4-(3H)-one,
2-n-butyl-5-(3'-pyrrolidinocarbonylmethyl)-6-methyl-3-[[2'-(1H-tetrazol-5-yl)biphenyl-4-yl]methyl]-pyrimidin-4-(3H)-one,
2-n-butyl-5-piperidinocarbonylmethyl-6-methyl-3-[[2'-(1H-tetrazol-5-yl)biphenyl-4-yl]methyl]-pyrimidin-4-(3H)-one,
2-n-butyl-5-piperidinocarbonylmethyl-6-methyl-1-[[2'-(1H-tetrazol-5-yl)biphenyl-4-yl]methyl]-pyrimidin-4-(1H)-one,
2-n-butyl-5-(4'-benzylpiperidinocarbonylmethyl)-6-methyl-3-[[2'-(1H-tetrazol-5-yl)biphenyl-4-yl]methyl]-pyrimidin-4-(3H)-one,
2-n-butyl-5-(4'-methylpiperidinocarbonylmethyl)-6-methyl-3-[[2'-(1H-tetrazol-5-yl)biphenyl-4-yl]methyl]-pyrimidin-4-(3H)-one,
2-n-butyl-5-(3',3'-dimethylpiperidinocarbonylmethyl)-6-methyl- 3-[[2'-(1H-tetrazol-5-yl)biphenyl-4-yl]methyl]-pyrimidin-4-(3H)-one,
2-n-butyl-5-(cis-2',6'-dimethylpiperidinocarbonylmethyl)-6-methyl-3-[[2'-(1H-tetrazol-5-yl)biphenyl-4-yl]methyl]-pyrimidin-4-(3H)-one,
2-n-butyl-5-(4'-ethoxycarbonylpiperidinocarbonylmethyl)-6-methyl-3-[[2'-(1H-tetrazol-5-yl)biphenyl-4-yl]methyl]-pyrimidin-4-(3H)-one,
2-n-butyl-5-(3'-ethoxycarbonylpiperidinocarbonylmethyl)-6-methyl-3-[[2'-(1H-tetrazol-5-yl)biphenyl-4-yl]methyl]-pyrimidin-4-(3H)-one,
2-n-butyl-5-(2'-ethoxycarbonylpiperidinocarbonylmethyl)-6-methyl- 3-[[2'-(1H-tetrazol-5-yl)biphenyl-4-yl]methyl]-pyrimidin-4-(3H)-one, 2-n-butyl-5-(4'-aminocarbonylpiperidinocarbonylmethyl)-6-methyl-3-[[2'-(1H-tetrazol-5-yl)biphenyl-4-yl]methyl]-pyrimidin-4-(3H)-one, 2-n-butyl-5-(3'-diethylaminocarbonylpiperidinocarbonylmethyl)-6-methyl-3-[[2'-(1H-tetrazol-5-yl)biphenyl-4-yl]methyl]-pyrimidin-4-(3H)-one, 2-n-butyl-5-hexamethyleneiminocarbonylmethyl-6-methyl-3-[[2'-(1H-tetrazol-5-yl)biphenyl-4-yl]methyl]-pyrimidin-4-(3H)-one, 2-n-butyl-5-heptamethyleneiminocarbonylmethyl-6-methyl-3-[[2'-(1H-tetrazol-5-yl)biphenyl-4-yl]methyl]-pyrimidin-4-(3H)-one, 2-n-butyl-5-(2'-pyrrolidinocarbonylethyl)-6-methyl-3-[[2'-(1H-tetrazol-5-yl)biphenyl-4-yl]methyl]-pyrimidin-4-(3H)-one, 2-n-butyl-5-[2'-((S)-2"-methoxycarbonylpyrrolidino)carbonylethyl]-6-methyl-3-[[2'-(1H-tetrazol-5-yl)biphenyl-4-yl]-methyl]-pyrimidin-4-(3H)-one, 2-n-butyl-5-[2'-((S)-2"-aminocarbonylpyrrolidino)carbonylethyl]-6-methyl-3-[[2'-(1H-tetrazol-5-yl)biphenyl-4-yl]methyl]-pyrimidin-4-(3H)-one, 2-n-butyl-5-[2'-(3"-pyrrolino)carbonylethyl]-6-methyl-3-[[2'-(1H-tetrazol-5-yl)biphenyl-4-yl]methyl]-pyrimidin-4-(3H)-one, 2-n-butyl-5-[2'-piperidinocarbonylethyl]-6-methyl-3-[[2'-(1H-tetrazol-5-yl)biphenyl-4-yl]methyl]-pyrimidin-4-(3H)-one, 2-n-butyl-5-[2'-(4"-benzylpiperidino)carbonylethyl]-6-methyl-3-[[2'-(1H-tetrazol-5-yl)biphenyl-4-yl]methyl]-pyrimidin-4-(3H)-one, 2-n-butyl-5-[2'-(4"-methylpiperidino)carbonylethyl]-6-methyl-3-[[2'-(1H-tetrazol-5-yl)biphenyl-4-yl]methyl]-pyrimidin-4-(3H)-one, 2-n-butyl-5-[2'-(3",3"-dimethylpiperidino)carbonylethyl]-6-methyl-3-[[2'-(1H-tetrazol-5-yl)biphenyl-4-yl]methyl]-pyrimidin-4-(3H)-one, 2-n-butyl-5-[2'-(4"-ethoxycarbonylpiperidino)carbonylethyl]-6-methyl-3-[[2'-(1H-tetrazol-5-yl)biphenyl-4-yl]methyl]-pyrimidin-4-(3H)-one, 2-n-butyl-5-[2'-(2"-ethoxycarbonylpiperidino)carbonylethyl]-6-methyl-3-[[2'-(1H-tetrazol-5-yl)biphenyl-4-yl]methyl]-pyrimidin-4-(3H)-one, 2-n-butyl-5-[2'-(4"-aminocarbonylpiperidino)carbonylethyl]-6-methyl-3-[[2'-(1H-tetrazol-5-yl)biphenyl-4-yl]methyl]-pyrimidin-4-(3H)-one, 2-n-butyl-5-[2'-(3"-diethylaminocarbonylpiperidino)carbonylethyl]-6-methyl-3-[[2'-(1H-tetrazol-5-yl)biphenyl-4-yl]methyl]-pyrimidin-4-(3H)-one, 2-n-butyl-5-(2'-hexamethyleneiminocarbonylethyl)-6-methyl-3-[[2'-(1H-tetrazol-5-yl)biphenyl-4-yl]methyl]-pyrimidin-4-(3H)-one, 2-n-butyl-5-(2'-heptamethyleneiminocarbonylethyl)-6-methyl-3-[[2'-(1H-tetrazol-5-yl)biphenyl-4-yl]methyl]-pyrimidin-4-(3H)-one, and the pharmaceutically acceptable salts thereof.

6. The compound of claim 1 wherein said compound is the one selected from the group consisting of:

2-n-butyl-5-thiazolidinocarbonylmethyl-6-methyl-3-[[2'-(1H-tetrazol-5-yl)biphenyl-4-yl]methyl]-pyrimidin-4-(3H)-one, 2-n-butyl-5-morpholinocarbonylmethyl-6-methyl-3-[[2'-(1H-tetrazol-5-yl)biphenyl-4-yl]methyl]-pyrimidin-4-(3H)-one, 2-n-butyl-5-(3',5'-dimethylmorpholinocarbonylmethyl)-6-methyl-3-[[2'-(1H-tetrazol-5-yl)biphenyl-4-yl]methyl]-pyrimidin-4-(3H)-one, 2-n-butyl-5-thiomorpholinocarbonylmethyl-6-methyl-3-[[2'-(1H-tetrazol-5-yl)biphenyl-4-yl]methyl]-pyrimidin-4-(3H)-one, 2-n-butyl-5-(4'-methylpiperazinocarbonylmethyl)-6-methyl-3-[[2'-(1H-tetrazol-5-yl)biphenyl-4-yl]methyl]-pyrimidin-4-(3H)-one, 2-n-butyl-5-(4'-acetylpiperazinocarbonylmethyl)-6-methyl-3-[[2'-(1H-tetrazol-5-yl)biphenyl-4-yl]methyl]-pyrimidin-4-(3H)-one, 2-n-butyl-5-(2'-morpholinocarbonylethyl)-6-methyl-3-[[2'-(1H-tetrazol-5-yl)biphenyl-4-yl]methyl]-pyrimidin-4-(3H)-one, 2-n-butyl-5-[2'-(3",5"-dimethylmorpholino)carbonylethyl]-6-methyl-3-[[2'-(1H-tetrazol-5-yl)biphenyl-4-yl]methyl]-pyrimidin-4-(3H)-one, 2-n-butyl-5-(2'-thiomorpholinocarbonylethyl)-6-methyl-3-[[2'-(1H-tetrazol-5-yl)biphenyl-4-yl]methyl]-pyrimidin-4-(3H)-one, 2-n-butyl-5-[2'-(4"-acetylpiperazino)carbonylethyl]-6-methyl-3-[[2'-(1H-tetrazol-5-yl)biphenyl-4-yl]methyl]-pyrimidin-4-(3H)-one, 2-n-butyl-5-[2'-(4"-(2'"-pyridyl)piperazino)carbonylethyl]-6-methyl-3-[[2'-(1H-tetrazol-5-yl)biphenyl-4-yl]methyl]-pyrimidin-4-(3H)-one, 2-n-butyl-5-[2'-(4"-trans-cinnamylpiperazino)carbonylethyl]-6-methyl-3-[[2'-(1H-tetrazol-5-yl)biphenyl-4-yl]methyl]-pyrimidin-4-(3H)-one, and the pharmaceutically acceptable salts thereof.

7. The compound of claim 1, wherein said compound is selected from the group consisting of:

2-ethyl-5-diethylaminocarbonylmethyl-6-methyl-3-[[2'-(1H-tetrazol-5-yl)biphenyl-4-yl]methyl]-pyrimidin-4-(3H)-one, 2-ethyl-5-(2'-diethylaminocarbonylethyl)-6-methyl-3-[[2'-(1H-tetrazol-5-yl)biphenyl-4-yl]methyl]-pyrimidin-4-(3H)-one, 2-n-propyl-5-diethylaminocarbonylmethyl-6-methyl-3-[[2'-(1H-tetrazol-5-yl)biphenyl-4-yl]methyl]-pyrimidin-4-(3H)-one, 2-n-propyl-5-(2'-diethylaminocarbonylethyl)-6-methyl-3-[[2'-(1H-tetrazol-5-yl)biphenyl-4-yl]methyl]-pyrimidin-4-(3H)-one, 2-n-butyl-5-diethylaminocarbonylmethyl-6-methyl-3-[[2'-(1H-tetrazol-5-yl)biphenyl-4-yl]methyl]-pyrimidin-4-(3H)-one, 2-n-butyl-5-diethylaminocarbonylmethyl-6-methyl-3-[[2'-(1H-tetrazol-5-yl)biphenyl-4-yl]methyl]-pyrimidin-4-(3H)-one, 2-n-butyl-5-(2'-diethylaminocarbonylethyl)-6-methyl-3-[[2'-(1H-tetrazol-5-yl)biphenyl-4-yl]methyl]-pyrimidin-4-(3H)-one, 2-n-butyl-5-(2'-benzylaminocarbonylethyl)-6-methyl-3-[[2'-(1H-tetrazol-5-yl)biphenyl-4-yl]methyl]-pyrimidin-4-(3H)-one, 2-n-butyl-5-(3'-diethylaminocarbonylpropyl)-6-methyl-3-[[2'-(1H-tetrazol-5-yl)biphenyl-4-yl]methyl]-pyrimidin-4-(3H)-one and the pharmaceutically acceptable salts thereof.

8. The compound according to claim 1 and the pharmaceutically acceptable salts thereof, wherein said salts are inorganic salts obtainable by reacting corresponding pyrimidinone compounds (I) with hydroxides, carbonate or alcoholate of alkali or alkaline earth metals in $H_2O$, lower alcohols, tetrahydrofuran, or the mixture thereof.

9. A compound according to claim 1 and the pharmaceutically acceptable salts thereof, wherein said salts are organic salts obtainable by reacting corresponding pyrimidinone compounds (I) with organic amine in $H_2O$, lower alcohols, tetrahydrofuran, organic solvent or the mixture thereof.

10. A pharmaceutical composition for treating cardiovascular diseases caused by antagonizing angiotensin II which comprises a therapeutically effective amount of a compound according to claim 1 or a pharmaceutically acceptable salt thereof and pharmaceutically acceptable vehicle, excipient and/or binder.

* * * * *